(12) United States Patent
Paegle et al.

(10) Patent No.: US 7,029,876 B2
(45) Date of Patent: Apr. 18, 2006

(54) PROCESS FOR PRODUCTION OF POLYPEPTIDES

(75) Inventors: Eriks Sasha Paegle, Seattle, WA (US); Dorothea Reilly, San Francisco, CA (US); Daniel G. Yansura, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 703 days.

(21) Appl. No.: 10/080,866

(22) Filed: Feb. 22, 2002

(65) Prior Publication Data

US 2003/0109024 A1    Jun. 12, 2003

Related U.S. Application Data

(60) Provisional application No. 60/274,384, filed on Mar. 9, 2001.

(51) Int. Cl.
*C12P 21/00* (2006.01)
*C12N 15/63* (2006.01)

(52) U.S. Cl. .................. 435/69.1; 435/320.1; 435/69.6
(58) Field of Classification Search ............... 435/69.6, 435/320.1
See application file for complete search history.

(56) References Cited

U.S. PATENT DOCUMENTS

| | | | |
|---|---|---|---|
| 4,578,355 A | 3/1986 | Rosenberg | 435/317 |
| 5,162,217 A | 11/1992 | Hartman et al. | 435/189 |
| 5,256,546 A | 10/1993 | Aviv et al. | 435/69.4 |
| 5,354,846 A | 10/1994 | Kehoe | 530/350 |
| 5,374,520 A | 12/1994 | Milman | 435/5 |
| 5,401,658 A | 3/1995 | Fiers et al. | 435/252.33 |
| 5,618,715 A | 4/1997 | Shoyab et al. | 435/325 |
| 5,834,184 A | 11/1998 | Harada et al. | 435/6 |

FOREIGN PATENT DOCUMENTS

| | | |
|---|---|---|
| EP | 131843 | 1/1985 |
| EP | 314184 | 5/1989 |
| EP | 457676 | 1/1992 |
| EP | 691406 | 1/1996 |
| EP | 700997 | 3/1996 |
| EP | 838525 | 4/1998 |
| EP | 893502 | 1/1999 |
| JP | 9059299 | 3/1997 |
| WO | WO 85/02624 | 6/1985 |
| WO | WO 85/04418 | 10/1985 |
| WO | WO 88/06628 | 9/1988 |
| WO | WO 89/03886 | 5/1989 |

OTHER PUBLICATIONS

Hasan N, Szybalski W, Control of cloned gene expression by promoter iversion in vivo: cibstruction of improved vectors with a multiple cloning site and the ptac promoter, 1987, Gene, 56:145-151.*

Li S, Li F, Wu W, Tan W, Yu M, Chen J, Tao K, Expression in *Escherichia coli* and purification of human thrombopoietin, 1997, Biotechnol. Appl. Biochem. 26: 15-17.*

Clements DA, Wang JK, Dionne CA, Goldfarb M, Activation of fibroblast growth factor (FGF) receptors by recombinant human FGF-5, 1993, Oncogene, 8:1311-1316.*

Loizos and Darst., "Mapping Interactions of *Escherichia coli* GreB with RNA Polymerase and Ternary Elogation Complexes." *J. Bio. Chem.* 274(33) :23378-23386 (Aug. 1999).

Seltas et al., "Expression Plasmid with a Very Tight Two-Step Control: Int/att-Mediated Gene Inversion with Respect to the Stationary Promoter." *Gene.* 267:213-220 (Apr. 2001).

Shatzman and Rosenberg., "the pAS Vector System and Its Application to Heterologous Gene Expression in *Escherichia coli*." *Hepatology.* (Suppl. 1) 7(1):305-355 (Jan. 1987).

Beck et al., "Efficient Production of Active Human Manganese Superoxide Dismutase in *Escherichia coli*." *Biotechnology*, 6:930-935 (Aug. 1988).

Bielawski et al., "Construction of a DNA-Polymerase I Overproducing Plasmid and Isolation of the Enzyme." *Acta Biochim. Pol.* 34(1):29-34 (1987).

Borukhov and Goldfarb., "Purification and Assay of *Escherichia coli* Transcript Cleavage Factors GreA and GreB." *Meth. Enzymol.*, 274:315-326 (1996).

(Continued)

*Primary Examiner*—James Ketter
*Assistant Examiner*—Patrick S. Riggins
(74) *Attorney, Agent, or Firm*—Janet E. Hasak

(57) ABSTRACT

Vectors for producing polypeptides heterologous to prokaryotes are described comprising, along with the polypeptide-encoding nucleic acid, anti-termination nucleic acid that inhibits intragenic transcription termination with a non-lambda promoter therefor and/or nucleic acid encoding a GreA or GreB protein and a promoter therefor. Also described are processes for producing a heterologous polypeptide in prokaryotic host cells utilizing such elements to improve the quality and/or quantity of heterologous polypeptide produced.

30 Claims, 23 Drawing Sheets

OTHER PUBLICATIONS

Borukhov et al., "GreA Protein: A Transcription Elongation Factor From *Escherichia coli.*" *Proc. Natl. Acad. Sci. USA* 89:8899-8902 (Oct. 1992).

Borukhov et al., "Transcript Cleavage Factors from *E. coli.*" *Cell.* 72:459-466 (Feb. 1993).

Chauhan and Apirion., "The Gene for a Small Stable RNA (10Sa RNA) of *Escherichia coli.*" *Molecular Microbiology.* 3(11):1481-1485 (1989).

Darst et al., "Crystallization of GreA, A Transcript Cleavage Factor From *Escherichia coli.*" *J. Mol. Bio.* 242:582-585 (1994).

Das., "Transcription Antitermination by Lambda N Gene Product in a Well Defined Plasmid System." *Fed. Proc.* (72nd Anual Mtg. Amer. Soc. Bio. Chem.—Abstract 1291) 40(6):1764 (May 31-Jun. 4, 1981).

Erie et al., "Multiple RNA Polymerase Conformations and GreA: Control of the Fidelity of Transcription." *Science.* 262:867-873 (1993).

Feng et al., "GreA- Induced Transcript Cleavage in Transcription Complexes Containing *Escherichia coli* RNA Polymerase Is controlled by Multiple Factors, Including Nascent Transcript Location and Structure." *J. Bio. Chem.* 269:22282-22294 (1994).

Feng et al., "Interactions Between RNA Polymerase and Transcript Affect GreA- And Gre-B-Mediated Reverse Translocation." *J. Cell. Biochem. Suppl.* (Abstract L408) 18C:58 (1994).

Franklin and Bennett., "The "N" Protein of Bacteriophage Lambda, Defined by its DNA Sequence, Is Highly Basic." *Gene.* 8:107-119 (1979).

Franklin., "N Transcription Antitermination Proteins of Bacteriophages λ. φ21 and F22". *J. Mol. Bio.* 181:85-91 (1985).

Franklin., "Clustered Arginine Residues of Bacterlophage λ N Protein are Essential to Antitermination of Transcription, but Their Locale Cannot Compensate for boxB Loop Defects." *J. Mol. Bio.* 231:343-360 (1993).

Franklin., "conservation of Genome Form but not Sequence in the Transcription Antitermination Determinants of Bacteriophages λ, φand P22."*J. Mol. Bio.* 181:75-88 (1984).

Friedman and Olson., "Evidence that a Nucleotide Sequence, "boxA," Is Involved in the Action of the NusA Protein." *Cell.* 34:143-149 (1983).

Friedman et al., "Transcription-Dependent Competition for a Host Factor: The Function and Optimal Sequence of the Phage λboxA Transcription Antitermination Signal," *Genes Dev.* 4:2210-2222 (1990).

Garcia et al., "The *E. coli* dnaY Gene Encodes an Arginine Transfer RNA." *Cell.* 45:453-459 (1986).

Gatenby and Castleton., "Amplification of Miaze Ribulose Bisphosphate Carboxylase Large Subunit Synthesis in *E. coli* by Transcriptional Fusion with the Lambda N Operon." *Mol. Gen. Genet.* 185:424-429 (1982).

Greenblatt et al., "Transcriptional Antitermination." *Nature.* 364:401-406 (Jul. 1993).

Gu et al., "Nascent RNA Cleavage by Arrested RNA Polymerase II Does Not Require Upstream Translocation of the Elongation Complex on DNA." *J. Bio. Chem.* 268:25604-25616 (1993).

Guo and Price., "Mechanism of DmS-II-Mediated Pause Suppression by Drosophila RNA Polymerase II." *J. Bio. Chem.* 268:18762-18770 (1993).

Horiuchi et al., "Effects of pH on Expression and Stabilization of β-Galactosidase by Recombinant *E. coli* with a Thermally-Induced Expression System." *Biotechnology Lett.* 16:113-118 (1994).

Hsu et al., "*Escherichia coli* Transcript Cleavage Factors GreA and GreB Stimulate Promoter Escape and Gene Expression In Vivo and In Vitro." *Proc. Natl. Acad. Sci. USA* 92:11588-11592 (1995).

Hwang et al., "High Level Expression of Porcine Growth Hormone in *Escherichia coli* From an Expression Vector Containing Bacteriophage λ $P_{L \text{ and N Gene Untrasnlated Region.}}$" *Biochem. & Biophys. Res. Comm.* 173:711-717 (1990).

Izban and Luse., "Factor-Stimulated RNA Polymerase II Transcribes at Physiological Elongation Rates on Naked DNA but Very Poorly on Chromatin Templates." *J. Bio. Chem.* 267(19):13647-13655 (1992).

Izban and Luse., "SII-Facilitated Transcript Cleavage in RNA Polymerase II Complexes Stalled Early After Initiation Occurs in Primarily Dinucleotide Increments." *J. Bio. Chem.* 268(17):12864-12873 (1993).

Izban and Luse., "The Increment of SIM-Facilitated Transcript Cleavage Varies Dramatically Between Elongation Competent and Incompetent RNA Polymerase II Ternary Complexes." *J. Bio. Chem.* 268(17):12874-12885 (Jun. 1993).

Izban and Luse., "The RNA Polymerase II Ternary Complex Cleaves the Nascent Transcript in a 3'→ 5'Direction in the Presence of Elongation Factor SII." *Genes & Development* 6:1342-1356 (1992).

Kanasawa et al., "Optimization of β-Galactosidase Production by Recombinant *E. coli* with Thermo-Inducible Expression System." *IFAC Symp. Ser.* 10:255-258 (1992).

Kassavetis and Geiduschek., "RNA Polymerase Marching Backward." *Science.* 259:944-945 (Feb. 1993).

Keiler et al., "Role of a Peptide Tagging System in Degradation of Proteins Synthesized from Damaged Messenger RNA." *Science.* 271:990-993 (Feb. 1996).

Koulich et al., "Distinct Function on N and C-Terminal Domains of GreA, and *Escherichia coli* Transcript Cleavage Factor." *J. Mol. Biol.* 276:379-389 (1998).

Koulich et al., "Domain Organization of *Escherichia coli* Transcript cleavage Factors GreA and GreB." *J. Bio. Chem.* 272(11):7201-7210 (Mar. 1997).

Kovgan et al., "Cloning and Expression of the HTLV-III Virus Surface Protein Gene in *E. coli."* *Vopr. Virusol.* (English Abstract Included) 31:485-489 (1986).

Lazinski et al., "Sequence-Specific Recognition of RNA Hairpins by bacteriophage Antiterminators Requires a Conserved Arginine-Rich Motif." *Cell.* 59:207-218 (Oct. 1989).

Lee et al., "GreA-Induced Transcript Cleavage Is Accompanied by Reverse Translocation to a Different Transcription Complex Conformation." *J. Bio. Chem.* 269 (35):22295-22303 (1994).

Li et al., "Antitermination of *E. coli* rRNA Transcription Is Caused by a Control Region Segment Containing Lambda nut-Like Sequences." *Cell.* 38:851-860 (Oct. 1984).

Lu et al., "Identification of greA Encoding a Transcriptional Elongation Factor as a Member of the carA-orf-carB-greA Operon in *Pseudomonas aeruginosa* PA01." *J. Bacteriology.* 179:3043-3046 (1997).

Makrides., "Strategies for Achieving High-Level Expression of Genes in *Escherichia coli."* *Microbiol. Rev.* 60(3):512-538 (1996).

Marks and Wood., "Nucleotide Sequence of the Rickettsia Prowazekil greA Homolog." *Nucleic Acids Research.* 20 (14):3785 (1992).

Martin-Gallardo et al., "Expression of the G Glycoprotein Gene of Human Respiratory Syncytial Virus in *Salmonella typhimurium.*" *J. Gen. Virol.* 74:453-458 (1993).
Mertens et al., "Tight Transcriptional Control Mechanism Ensures Stable High-Level Expression from T7 Promoter-Based Expression Plasmids." *Biotechnology.* 13:175-179 (Feb. 1995).
Mogridge et al., "Involvement of boxA Nucleotides in the Formation of a Stable Ribonucleoprotein Complex Containing the Bacteriophage ϕ N Protein." *J. Bio. Chem.* 273(7): 4143-4148 (1998).
Mote and Reines., "Recognition of a Human Arrest Site Is Conserved Between RNA Polymerase II and Prokaryotic RNA Polymerases." *J. Bio. Chem.* 273*27):16843-16852 (1998).
Olson et al., "Analysis of nutR: A Region of Phage Lambda Required for Antitermination of Transcription." *Cell.* 31:61-70 (Nov. 1982).
Orlova et al., "Intrinsic Transcript Cleavage Activity of RNA Polymerase." *Proc. Natl. Acad. Sci. USA* 92:4596-4600 (May 1995).
Patterson et al., "Bacteriophage Lambda N-Dependent Transcription Antitermination: Competition for an RNA Site May Regulate Antitermination." *J. Mol. Bio.* 236:217-228 (1994).
Polyakov et al., "Visualization of the Binding Site for the Transcript Cleavage Factor GreB on *Escherichia coli* RNA Polymerase." *J. Mol. Bio.* 281:465-473 (1998).
Rees et al., "Bacteriophage λ N Protein Alone Can Induce Transcription Antitermination In Vitro." *Proc. Natl. Acad. Sci. USA* 93:342-346 (Jan. 1996).
Reines et al., "Transcription Elongation Factor SII (TFIIS) Enables RNA Polymerase II to Elongate Through a Block to Transcription in a Human Gene In Vitro." *J. Bio. Chem.* 264(18):10799-10809 (Jun. 1989).
Reines., "Elongation Factor-Dependent Transcript Shortening by Template-Engaged RNA Polymerase II." *J. Bio. Chem.* 267(6):3795-3800 (Feb. 1992).
Schauer et al., "ϕ N Antitermination System: Functional Analysis of Phage Interactions with the Host NusA Protein." *J. Mol. Bio.* 194:679-690 (1987).
Sluder et al., "Properties of a Drosophila RNA Polymerase II Elongation Factor." *J. Bio. Chem.* 264(15):8963-8969 (May 1989).
Stanssens et al., "Inefficient Translation Initiation Causes Premature Transcription Termination in the lacZ Gene." *Cell.* 44:711-718 (Mar. 1986).
Stebbins et al., "Crystal Structure of the GreA Transcript Cleavage Factor From *Escherichia coli.*" *Nature.* 373(16): 636-640 (Feb. 1995).
Surratt et al., "Spontaneous Cleavage of RNA in Ternary Complexes of *Escherichia coli* RNA Polymerase and its Significance for the Mechanism of Transcription." *Proc. Natl. Acad. Sci. USA* 88:7983-7987 (Sep. 1991).
Tu et al., "C-Terminal Extension of Truncated Recombinant Proteins in *Escherichia coli* with a 10Sa RNA Decapeptide." *J. Bio. Chem.* 270(16):9322-9326 (Apr. 1995).
Wang and Hawley., "Indentification of a 3' 3' → 5' Exonuclease Activity Associated with Human RNA Polymerase II." *Proc. Natl. Acad. Sci. USA.* 90:843-847 (Feb. 1993).
Weisberg and Gottesman., "Processive Antitermination." *J. Bacteriol.* 181(2):359-367 (Jan. 1999).
Zhukovskaya et al., "Inactive $O^6$-Methylguanine-DNA Methyltransferase in Human Cells." *Nucleic Acids Research.* 20(22):6081-6090 (1992).
Oondon, Ciaran, et al., "Control of rRNA Transcription in *Escherichia coli*" *Microbiological Reviews* 59(4):623-645 (Dec. 1995).
McKenney, K., et al., "A System to Study Promoter and Terminator Signals Recognized by *Escherichia coli* RNA Polymerase" *Gene Amplification and Analysis*, Jack G. Chirikjian and Takis S. Papas1981 vol. 2:383-415 (1981).
Podhajska, A. J., et al., "Control of cloned gene expression by promoter inversion in vivo: construction of the heat-pulse-activated att-nutL-p-att-N module" *Gene* 40:163-168 (1985).
Richardson and Greenblatt, "Control of RNA chain elongation and termination" *Escherichia coli and Salmonella: cellular and molecular biology*, Washington, DC:ASM Press vol. 1:822-848 (1996).

* cited by examiner pJJ142 digest with XbaI and PstI, isolate large frag.

PCR reaction digest PCR reaction with XbaI and PstI, isolate 491 bp frag.

ligate pDR3

SEQUENCE LISTING

<160> NUMBER OF SEQ ID NOS: 19

<210> SEQ ID NO 1
<211> LENGTH: 80
<212> TYPE: DNA
<213> ORGANISM: Artificial sequence
<220> FEATURE:
<223> OTHER INFORMATION: Expression construct

<400> SEQUENCE: 1
ttaactagta cgcaacgctc ttacacattc cagccctgaa aaagggcaaa          50
gttcacgtaa aaaggatatc tagaattatg                                80

<210> SEQ ID NO 2
<211> LENGTH: 114
<212> TYPE: DNA
<213> ORGANISM: Artificial sequence
<220> FEATURE:
<223> OTHER INFORMATION: Expression construct

<400> SEQUENCE: 2
tatagtcgct ttgtttttat tttttaatgt atttgtaact agtacgcaac          50
gctcttacac attccagccc tgaaaaaggg caaagttcac gtaaaaagga         100
tatctagaat tatg                                                114

<210> SEQ ID NO 3
<211> LENGTH: 5
<212> TYPE: PRT
<213> ORGANISM: Artificial sequence
<220> FEATURE:
<223> OTHER INFORMATION: Fragment of phage lambda N

<400> SEQUENCE: 3

Met Asp Ala Gln Thr
 1               5

<210> SEQ ID NO 4
<211> LENGTH: 56
<212> TYPE: DNA
<213> ORGANISM: Artificial sequence
<220> FEATURE:
<223> OTHER INFORMATION: E. coli and phage lambda N fragment fusion

<400> SEQUENCE: 4
tttaatgtgt ggaattgtga gcggataaca attaagcttt tatggatgca          50
caaaca                                                          56

<210> SEQ ID NO 5
<211> LENGTH: 68
<212> TYPE: DNA
<213> ORGANISM: Artificial sequence
<220> FEATURE:
<223> OTHER INFORMATION: E. coli and phage lambda N fragment fusion

<400> SEQUENCE: 5
tttaatgtgt ggaattgtga gcggataaca attaagctta ggattctaga          50
attatggatg cacaaaca                                             68

<210> SEQ ID NO 6
<211> LENGTH: 4
<212> TYPE: PRT

<213> ORGANISM: Homo sapiens

<400> SEQUENCE: 6

Ile Glu Pro Arg
 1

<210> SEQ ID NO 7
<211> LENGTH: 60
<212> TYPE: DNA
<213> ORGANISM: Artificial sequence
<220> FEATURE:
<223> OTHER INFORMATION: Fragment for plasmid construction

<400> SEQUENCE: 7
ctagttaact agtacgcatt ccagccctga aaagggcaa agttcacgta         50 aaaaggatat                                                   60

<210> SEQ ID NO 8
<211> LENGTH: 60
<212> TYPE: DNA
<213> ORGANISM: Artificial sequence
<220> FEATURE:
<223> OTHER INFORMATION: Fragment for plasmid construction

<400> SEQUENCE: 8
ctagatatcc tttttacgtg aactttgccc ttttcaggg ctggaatgcg         50 tactagttaa                                                   60

<210> SEQ ID NO 9
<211> LENGTH: 40
<212> TYPE: DNA
<213> ORGANISM: Artificial sequence
<220> FEATURE:
<223> OTHER INFORMATION: Fragment for plasmid construction

<400> SEQUENCE: 9
ctgtctcagg aagggtaagc ttttatggat gcacaaacac                   40

<210> SEQ ID NO 10
<211> LENGTH: 47
<212> TYPE: DNA
<213> ORGANISM: Artificial sequence
<220> FEATURE:
<223> OTHER INFORMATION: Fragment for plasmid construction

<400> SEQUENCE: 10
cggcgtgttt gtgcatccat aaaagcttac ccttcctgag acagatt          47

<210> SEQ ID NO 11
<211> LENGTH: 35
<212> TYPE: DNA
<213> ORGANISM: Artificial sequence
<220> FEATURE:
<223> OTHER INFORMATION: Fragment for plasmid construction

<400> SEQUENCE: 11
agcttaggat tctagaatta tggatgcaca aacac                        35

<210> SEQ ID NO 12
<211> LENGTH: 35
<212> TYPE: DNA
<213> ORGANISM: Artificial sequence
<220> FEATURE:
<223> OTHER INFORMATION: Fragment for plasmid construction

```
<400> SEQUENCE: 12
cggcgtgttt gtgcatccat aattctagaa tccta                                35

<210> SEQ ID NO 13
<211> LENGTH: 73
<212> TYPE: DNA
<213> ORGANISM: Artificial sequence
<220> FEATURE:
<223> OTHER INFORMATION: Fragment for plasmid construction

<400> SEQUENCE: 13
ctagttaact agtacgcaac gctcttacac attccagccc tgaaaaaggg                50
caaagttcac gtaaaaagga tat                                             73

<210> SEQ ID NO 14
<211> LENGTH: 73
<212> TYPE: DNA
<213> ORGANISM: Artificial sequence
<220> FEATURE:
<223> OTHER INFORMATION: Fragment for plasmid construction

<400> SEQUENCE: 14
ctagatatcc ttttacgtg aactttgccc ttttcaggg ctggaatgtg                  50 taagagcgtt gcgtactagt taa                                             73

<210> SEQ ID NO 15
<211> LENGTH: 48
<212> TYPE: DNA
<213> ORGANISM: Artificial sequence
<220> FEATURE:
<223> OTHER INFORMATION: Primer

<400> SEQUENCE: 15
ccccccccct ctagaaaaat gaaaactcct ctggtaacgc gggaaggg                  48

<210> SEQ ID NO 16
<211> LENGTH: 39
<212> TYPE: DNA
<213> ORGANISM: Artificial sequence
<220> FEATURE:
<223> OTHER INFORMATION: Primer

<400> SEQUENCE: 16
cccccccccc tgcagttacg gtttcacgta ctcgatagc                            39

<210> SEQ ID NO 17
<211> LENGTH: 44
<212> TYPE: DNA
<213> ORGANISM: Artificial sequence
<220> FEATURE:
<223> OTHER INFORMATION: Primer

<400> SEQUENCE: 17
ccccccccct ctagaattct atgcaagcta ttccgatgac ctta                      44

<210> SEQ ID NO 18
<211> LENGTH: 36
<212> TYPE: DNA
<213> ORGANISM: Artificial sequence
<220> FEATURE:
<223> OTHER INFORMATION: Primer

<400> SEQUENCE: 18
cccccccccc tgcagttaca ggtattccac cttaat                               36
```

-continued

```
<210> SEQ ID NO 19
<211> LENGTH: 12
<212> TYPE: PRT
<213> ORGANISM: Artificial sequence
<220> FEATURE:
<223> OTHER INFORMATION: Peptide for generating antibodies

<400> SEQUENCE: 19

Cys Ala Ala Asn Asp Glu Asn Tyr Ala Leu Ala Ala
 1               5                  10
```

PROCESS FOR PRODUCTION OF POLYPEPTIDES

RELATED APPLICATIONS

This application is a non-provisional application filed under 37 CFR 1.53(b) (1), claiming priority under 35 USC 119(e) to provisional application No. 60\274,384 filed Mar. 9, 2001, the contents of which are incorporated herein by reference.

BACKGROUND OF THE INVENTION

1. Field of the Invention

This invention relates to improved vectors and methods for producing polypeptides using such vectors. In particular, this invention is related to improved expression of polypeptides from nucleic acids such as cloned genes and production of various polypeptides and proteins, including those of eukaryotic origin in prokaryotic hosts.

2. Description of Related Art

The level of production of a protein in a host cell is governed by three major factors: the number of copies of its gene within the cell, the efficiency with which those gene copies are transcribed, and the efficiency with which the resultant messenger RNA (mRNA) is translated. The quality of protein produced is similarly governed by various factors, including the anti-termination mechanism in the host cell.

Recombinant proteins produced in *E. coli* occasionally contain structural modifications that restrict their usefulness as therapeutic drugs or reagents for structure-function relationship studies. Such modifications include N- and C-terminal truncations, extensions, incomplete removal of N-terminal initiator methionine, misincorporation of lysine for arginine, and norleucine for methionine. For example, during the purification of recombinant murine interleukin-6 from *E. coli*, it was observed that 5–10% of the mIL-6 molecules contained a novel C-terminal modification (Tu et al., *J. Biol. Chem.*, 270: 9322–9326 (1995)).

This C-terminal "tag" is encoded by a small metabolically stable RNA of *E. coli* (10Sa RNA) (Chauhan and Apirion, *Mol. Microbiol.*, 3: 1481–1485 (1989)). 10Sa RNA, also known as transfer-messenger RNA, or tmRNA, contains a tRNA-like structure in vivo with the 5'- and 3'-end sequences and an internal reading frame encoding a "tag" peptide.

The primary cause of the production of truncated 10Sa-tagged proteins is the translation of mRNA truncated within the coding region (Keiler et al., *Science*, 271: 990–993 (1996)). Premature transcription termination and RNase cleavage appear to be the major factors capable of producing such truncated mRNA. The first of these factors, premature transcription termination, is potentially amenable to some type of transcription anti-termination. Several of these systems have been described, including λN, λQ, HK022, rrn, and Psu (Weisberg et al., *J. Bacteriol.*, 181: 359–367 (1999)). Most of these systems are used to control gene expression temporally in phage development by transcribing through intergenic transcription terminators. The function of the rrn anti-termination is somewhat different, and it has been proposed to prevent rho-dependent transcription termination within the non-translated ribosomal RNA operons.

Despite the accumulation of considerable knowledge of these systems over many years, their only demonstrated usefulness in terms of recombinant technology has been in the control of gene expression by overriding intergenic transcriptional terminators (Mertens et al., *Bio/Technol.*, 13: 175–179 (1995)). Other reports describe the failure of one of these systems (rrn) to alleviate problems within a translated coding sequence containing extensive secondary structure (Makrides, *Microbiol. Rev.*, 60: 512–538 (1996)).

Several fusions of a protein with at least a portion of an anti-terminator protein have been disclosed, especially the N gene protein and most particularly the N-terminal fragment thereof (JP 9059299 published Mar. 4, 1997; WO 89/03886 published May 5, 1989; WO 88/06628 published Sep. 7, 1988; U.S. Pat. No. 5,834,184 issued Nov. 10, 1998; EP 700,997 published Mar. 13, 1996; U.S. Pat. No. 5,354,846 issued Oct. 11, 1994; U.S. Pat. No. 5,618,715 issued Apr. 8, 1997; U.S. Pat. No. 5,374,520 issued Dec. 20, 1994; Zhukovskaya et al., *Nucl. Acids. Res.*, 20: 6081–6090 (1992); Horiuchi et al., *Biotechnol. Lett.*, 16: 113–118 (1994); Kamasawa et al., *IFAC Symp. Ser.*, 10: 255–258 (1992); Kovgan et al., *Vopr. Virusol.*, 31: 485–489 (1986)).

Several plasmids that contain an N utilization site for binding anti-terminator N protein produced by the host cell, such as *E. coli*, have been constructed (U.S. Pat. No. 5,256,546 issued Oct. 26, 1993; EP 691,406 published Jan. 10, 1996; U.S. Pat. No. 5,162,217 issued Nov. 10, 1992; EP 131,843 published Jan. 23, 1985). Other plasmids involving the N gene, operon, or portion thereof have been described (SU 1405313 published Mar. 15, 1994; EP 314,184 published May 3, 1989; U.S. Pat. No. 4,578,355 issued Mar. 25, 1986; WO 85/04418 published Oct. 10, 1985; Rees et al., *Proc. Natl. Acad. Sci. USA*, 93: 342–346 (1996); Hwang et al., *Biochem. Biophys. Res. Commun.*, 173: 711–717 (1990); Bielawski et al., *Acta Biochim. Pol.*, 34: 29–34 (1987); Stanssens et al., *Cell*, 44: 711–718 (1986); Gatenby and Castleton, *Mol. Gen. Genet.*, 185: 424–429 (1982)); Martin-Gallardo et al., *J. Gen. Virol.*, 74: 453–458 (1993); Das, 72$^{nd}$ Annual Meeting of the American Society of Biological Chemists, May 31–Jun. 4, 1981, *Fed. Proc.*, 40 (6): 1764 (1981); Beck et al., *Bio/Technology*, 6: 930–935 (1988)).

The expression of gamma-interferon was found to increase over two-fold when the λN anti-termination system was eliminated and only the $P_L$ promoter was used (WO 85/02624 published Jun. 20, 1985). Cloning and expression vectors in which the active N gene is preferably absent are also described (U.S. Pat. No. 5,401,658 issued Mar. 28, 1995).

Transcription of DNA is often arrested at sites in DNA that trap a fraction of elongating RNA polymerase molecules that pass through, resulting in locked ternary complexes that cannot propagate or dissociate their RNA product. Transcript cleavage factors cleave the RNA in such complexes at the 3' end, allowing RNA polymerase to back up and re-attempt to read through the potential trap. In addition to assuring efficient transcript elongation, transcript cleavage factors increase the fidelity of transcription, since misincorporated bases at the 3' end of the nascent RNA also lead to arrested complexes (Erie et al., *Science*, 262: 867–873 (1993)). Further, such factors allow RNA polymerase to transcribe through strong blocks to elongation that can otherwise arrest the enzyme on the DNA (Lee et al., *J. Biol. Chem.*, 269: 22295–22303 (1994)). In addition, these factors can facilitate the transition of RNA from the stage of abortive initiation to elongation at certain promoters (Hsu et al., *Proc. Natl. Acad. Sci. USA*, 92: 11588–11592 (1995)).

Both bacteria and eukaryotes contain proteins that can stimulate such cleavage (Surratt et al., *Proc. Natl. Acad. Sci. USA*, 88: 7983–7987 (1991); Borukhov et al., *Proc. Natl. Acad. Sci. USA*, 89: 8899–8902 (1992); Borukhov et al., *Cell*, 72: 459–466 (1993); Izban and Luse, *Genes & Dev.*, 6: 1342–1356 (1992); Izban and Luse, *J. Biol. Chem.*, 267:

13647–13655 (1992); Izban and Luse, *J. Biol. Chem.*, 268: 12864–12873 (1993); Izban and Luse, *J. Biol. Chem.*, 268: 12874–12885 (1993); Kassavetis and Geiduschek, *Science*, 259: 944–945 (1993); Reines, *J. Biol. Chem.*, 267: 3795–3800 (1992); Wang and Hawley, *Proc. Natl. Acad. Sci. USA*, 90: 843–847 (1993); Gu et al., *J. Biol. Chem.*, 268: 25604–25616 (1993); Guo and Price, *J. Biol. Chem.*, 268: 18762–18770 (1993)). Two modes of cleavage have been described. One yields one to three nucleotide fragments and the other produces larger fragments, up to at least 12 nucleotides in size. Two transcript cleavage factors, GreA and GreB, have been identified in *E. coli* (Borukhov et al., *Proc. Natl. Acad. Sci. USA*, supra, and Borukhov et al., *Cell*, supra, respectively). GreA-dependent transcript cleavage usually results in the removal of di- and trinucleotides from the 3' end of the stalled RNA. GreB-dependent cleavage yields larger oligonucleotides, up to a length of nine nucleotides. Both proteins bind RNA polymerase. Neither the GreA nor GreB proteins possess intrinsic nuclease activity; rather, they stimulate a nuclease activity inherent in RNA polymerase (Oriova et al., *Proc. Natl. Acad. Sci. USA*, 92: 4596–4600 (1995)). The GreA and GreB proteins are homologous, sharing 38% sequence identity and 59% sequence similarity. It was found that GreA-induced transcript cleavage in transcription complexes containing *E. coli* RNA polymerase is controlled by multiple factors, including nascent transcript location and structure (Feng et al., *J. Biol. Chem.*, 269: 22282–22294 (1994)).

Crystallization of GreA has been disclosed (Darst et al., *J. Mol. Biol.*, 242: 582–585 (1994)) as well as its crystal structure (Stebbins et al., *Nature*, 373: 636–640 (1995)). The organization and functions of domains of GreA and/or GreB have been investigated (Koulich et al., *J. Biol. Chem.*, 272: 7201–7210 (1997); Koulich et al., *J. Mol. Biol.*, 276: 379–389 (1998); Polyakov et al., *J. Mol. Biol.*, 281: 465–473 (1998)). Moreover, purification and assay procedures for GreA and GreB are reported (Borukhov and Goldfarb, *Meth. Enzymol.*, 274: 315–326 (1996)). Interactions between RNA polymerase and transcript affect GreA- and GreB-mediated reverse translocation (Feng et al., *J. Cellular Biochem. Suppl.*, 0: 18C, p. 58 (1994)). Both GreA and GreB have been shown to enhance promoter escape (Hsu et al., *Proc. Natl. Acad. Sci. USA*, 92: 11588–11592 (1995)).

In eukaryotes, the transcription elongation factor TFIIS, otherwise known as SII (Reines et al., *J. Biol. Chem.*, 264: 10799–10809 (1989); Sluder et al., *J. Biol. Chem.*, 264: 8963–8969 (1989)), is similar to the GreA and GreB proteins in that it stimulates RNA cleavage from the 3' end of RNA in a stalled complex but does not share significant sequence homology with the GreA and GreB proteins (Borukhov et al., *Cell*, supra). TFIIS stimulates either small- or large-fragment cleavage, depending on reaction conditions and the particular complex examined (Izban and Luse, *J. Biol. Chem.*, 268: 12874–12885 (1993), supra; Wang and Hawley, supra). Evidence for functional similarity between prokaryotic and eukaryotic transcription elongation and readthrough mechanisms has been found (Mote and Reines, *J. Biol. Chem.*, 273: 16843–16852 (1998)).

Homologs of *E. coli* GreA have been identified. The predicted amino acid sequence encoded by the *Rickettsia prowazekii* greA gene has 50.3% amino acid identity and 66.9% amino acid similarity to *E. coli* GreA (Marks and Wood, *Nucl. Acids Res.*, 20: 3785 (1992)). The deduced amino acid sequence of GreA from *Pseudomonas aeruginosa* exhibits 65.2% identity to its counterpart in *E. coli* K-12 (Lu et al., *J. Bacteriol.*, 179: 3043–3046 (1997)). *Streptococcus pneumoniae* polypeptide GreA has also been disclosed, along with methods of producing the GreA polypeptide by recombinant means and for utilizing GreA or its antagonists for the treatment or diagnosis of infection (EP 838,525 published Apr. 2, 1998). Further, GreA from *Staphylococcus aureus* has also been disclosed, as well as recombinant methods of making it and methods for utilizing it to screen for antibacterial compounds (EP 893,502 published Jan. 27, 1999).

There is a current and continuing need in the art for improving the quality of recombinant protein produced by host cells such that production of truncated forms of the protein, such as 10Sa-tagged material, is minimized or eliminated. There is also a need for higher amounts of full-length protein produced by prokaryotes.

SUMMARY OF THE INVENTION

Accordingly, the present invention provides, in one aspect, a vector for producing a polypeptide heterologous to prokaryotic cells comprising (1) anti-termination nucleic acid that inhibits intragenic transcription termination with a non-lambda promoter therefor, and (2) RNA encoding the polypeptide with a non-lambda promoter therefor, wherein an RNA recognition site for binding anti-termination protein produced from the nucleic acid is located 5' of the RNA encoding the polypeptide. Preferably, the vector further comprises nucleic acid encoding a GreA or GreB protein with a promoter therefor.

In another aspect, the invention provides a process for producing a heterologous polypeptide in prokaryotic host cells comprising:

(a) culturing the host cells, which comprise (1) anti-termination nucleic acid that inhibits intragenic transcription termination with a non-lambda promoter therefor, and (2) RNA encoding the polypeptide with a non-lambda promoter therefor, wherein an RNA recognition site for binding anti-termination protein produced from the nucleic acid is located 5' of the RNA encoding the polypeptide, and wherein the anti-termination nucleic acid is expressed at the time of expression of the RNA; and (b) recovering the heterologous polypeptide from the cells or from cell culture medium.

The invention supplies, in yet another aspect, a vector comprising nucleic acid encoding GreA or GreB protein and nucleic acid encoding a polypeptide heterologous to prokaryotic cells, preferably with one or more promoters for the nucleic acids.

In a still further aspect, the invention entails a process for producing a heterologous polypeptide in prokaryotic host cells comprising:

(a) culturing the host cells, which comprise nucleic acid encoding GreA or GreB protein and nucleic acid encoding the heterologous polypeptide, and one or more promoters for the nucleic acids; and (b) recovering the heterologous polypeptide from the cells or from cell culture medium.

Lambda phage uses N anti-termination to control gene expression by transcribing through strategically placed intergenic terminators. The anti-termination system herein is found to be effective against intragenic termination signals within heterologous genes.

Moreover, the general trend in the literature over the years is to eliminate the lambda N anti-termination system that was used with the adjacent $P_L$ promoter system and just use the $P_L$ promoter or replace the N gene with a polylinker or other fusion partner. In contrast, the invention herein lies in using the anti-termination system without the $P_L$ promoter.

Further, the system herein is designed specifically to prevent the formation and accumulation of truncated and 10Sa-tagged heterologous proteins, which cause problems with protein purification. One of the primary causes of truncated and 10Sa-tagged proteins is premature transcription termination within a translated coding sequence. The accumulation of full-length protein may be similar with or without the anti-termination system, but the accumulation of the truncated forms is significantly reduced by promoting transcriptional readthrough of intragenic termination signals within the protein's coding sequence.

Additionally, unwanted cleavage of the polypeptide is minimized by inclusion of nucleic acids encoding GreA or GreB.

BRIEF DESCRIPTION OF THE DRAWINGS

FIG. 16A is a Coomassie blue-stained SDS gel of whole cell extracts;
FIG. 16B is a histidine/horse-radish-peroxidase (HRP)-probed blot of whole cell extracts (the whole cell lysate is separated by SDS-PAGE, transferred to nitrocellulose, and probed with an agent that binds to the polyhis motif on the TPO leader);
and FIG. 16C is an anti-10Sa polyclonal antibody Western blot of whole cell extracts from TPO induction cultures. The arrows point to full-length TPO.

FIG. 19A is a Coomassie blue-stained SDS gel of whole cell extracts; FIG. 19B is a histidine/horse-radish-peroxidase (HRP)-probed blot of whole cell extracts; and FIG. 19C is an anti-10Sa polyclonal Western blot of whole cell extracts. The arrows point to full-length TPO.

FIG. 20A is a Coomassie blue-stained SDS gel of whole cell extracts; FIG. 20B is a histidine/horse-radish-peroxidase (HRP)-probed blot of whole cell extracts; and FIG. 20C is an anti-10Sa polyclonal antibody Western blot of whole cell extracts. The arrows point to full-length TPO.

FIG. 22 shows the construction of plasmid pFGF5IT-AT.
FIG. 23A is a Coomassie blue-stained SDS gel of whole cell lysates from induced fermentation cultures (equivalent O.D.$_{600}$);
FIG. 23B is a Western blot of whole cell lysates probed with an anti-FGF-5 antibody;
and FIG. 23C is a Western blot of whole cell lysates probed with an anti-10Sa antibody. The arrows point to full-length FGF-5.

DESCRIPTION OF THE PREFERRED EMBODIMENTS

Figure 1:
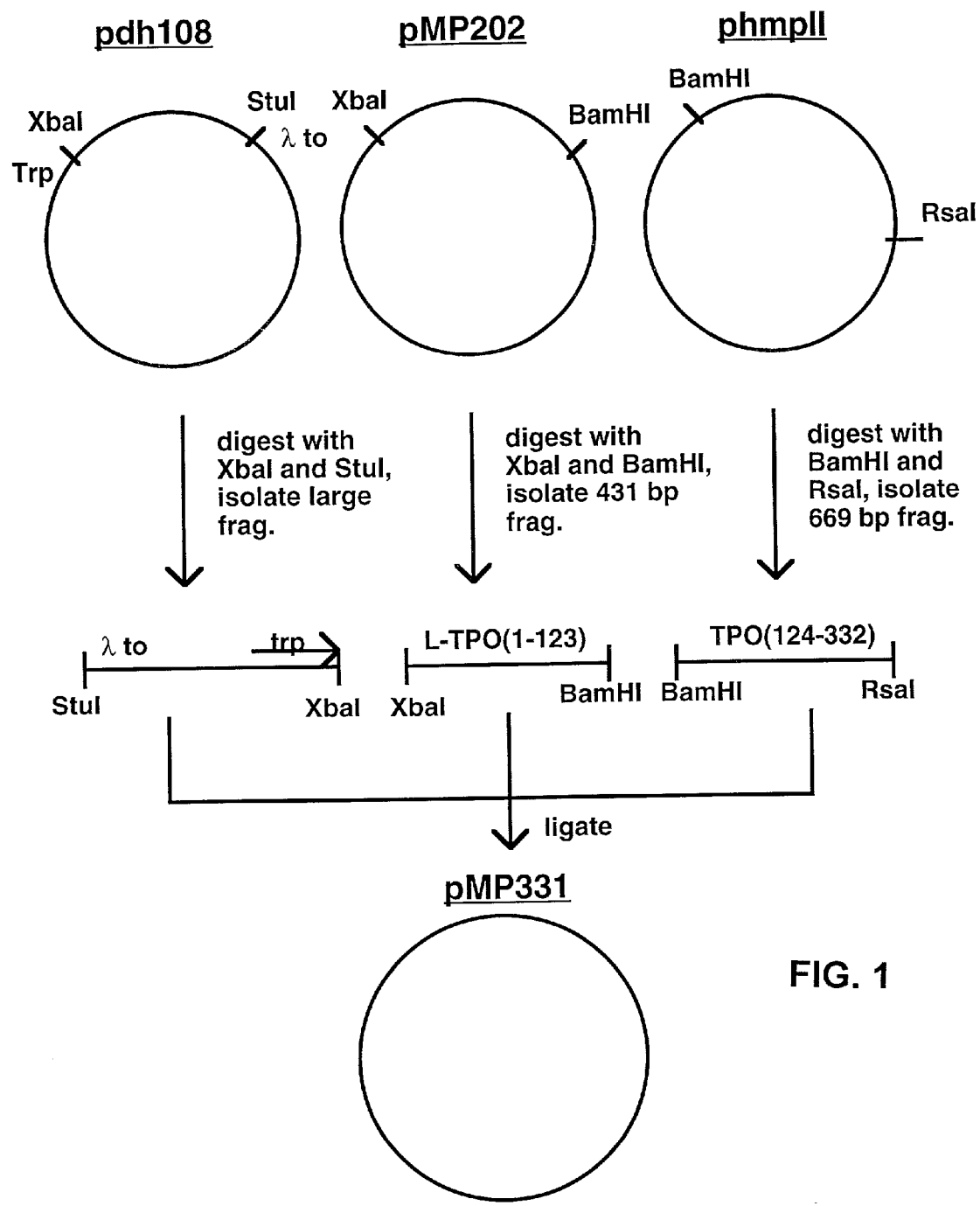
FIG. 1 shows the construction of plasmid pMP331.

As used herein, "greA" and "greB" refer to genes encoding the transcript cleavage factors known in the literature as GreA and GreB proteins, respectively, and amino acid sequence variants thereof that are functional and effective for the same purpose of transcript cleavage useful in the invention disclosed herein. They may be from any source, with one example being the greA and greB genes from *E. coli* as described by Borukhov et al., *Proc. Natl. Acad. Sci. USA*, supra, and Borukhov et al., *Cell*, supra, and another example being the greA genes disclosed by EP 838,525.

As used herein, "anti-termination factor" is an anti-terminator protein that generally has RNA binding activity and anti-terminator activity. Examples include the anti-terminator N proteins of phages λ, φ21, and P22, which have been completely sequenced. See Franklin, *J. Mol. Biol.*, 181: 85–91 (1985) and Lazinski et al., *Cell*, 59: 207–218 (1989). All of these N proteins contain an arginine-rich domain corresponding to about amino acids 1–19 at the N-terminus of the protein that is responsible for RNA binding activity of these proteins, while the remainder of each protein confers anti-terminator activity (Franklin, *J. Mol. Biol.*, 231: 343–360 (1993)). Preferably, the anti-termination factor is a phage factor. More preferably it is a λN or λQ gene, more preferably a phage λN protein.

An "RNA recognition site" refers to a site on an RNA molecule that recognizes a specific protein. For example, an RNA recognition site for binding anti-termination protein would be nut for the N gene, and qut for the Q gene.

A "transcriptional terminator" or "transcriptional termination signal" is operationally defined as a point where the rate of release of an RNA transcript is greater than the rate of addition of the next nucleotide. For purposes herein, the terminator may be rho-dependent or rho-independent. An "intragenic" terminator is one that is homologous to the heterologous polypeptide coding sequence herein. An "intergenic" terminator is one that is exogenous to the heterologous polypeptide coding sequence herein, for example, bacterial or bacteriophage termination signals when the polypeptide is mammalian in origin.

"Anti-termination nucleic acid that inhibits intragenic transcription termination" signifies nucleic acid encoding anti-termination factors that block or override intragenic transcriptional terminators within heterologous genes. This definition includes the N and Q genes, as well as rrn and HK022 anti-termination nucleic acid. Preferably, it is the N or Q gene.

As used herein, "cistron" is a distinctly translatable sequence defined by having a single messenger RNA transcript with one promoter.

As used herein, "polycistronic" refers to a polynucleotide comprising two or more cistrons where several different genes are transcribed as a single message from their operons, and two or more pairs of start and stop codons.

As used herein, "polypeptide" or "polypeptide of interest" refers generally to peptides and proteins having more than about ten amino acids. The polypeptides are "heterologous," i.e., foreign to the host cell being utilized, such as a human protein produced by a bacterial cell, or a bacterial polypeptide produced from a bacterial cell line that is not the native source of the polypeptide. Preferably, the polypeptide is mammalian, and most preferably human.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNASE; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3,-4,-5, or -6 (NT-3, NT-4, NT-5, or NT-6), or a nerve growth factor such as NGF-α; cardiotrophins (cardiac hypertrophy factor) such as cardiotrophin-1 (CT-1); platelet-derived growth factor (PDGF); fibroblast growth factors such as aFGF, bFGF, and FGF-5; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, CD-19, CD-20, and CD-40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

Preferred mammalian polypeptides include t-PA, gp120, anti-HER-2, anti-CD20, anti-CD11a, anti-CD18, anti-CD40, DNase, IGF-I, IGF-II, FGF-5, thrombopoietin, brain IGF-I, growth hormone, relaxin chains, growth hormone releasing factor, insulin chains or pro-insulin, urokinase, immunotoxins, neurotrophins, and antigens. Particularly preferred mammalian polypeptides include, e.g., t-PA, gp120(IIIb), anti-HER-2, anti-CD20, anti-CD11a, anti-CD18, anti-CD40, DNase, thrombopoietin, IGF-I, IGF-II, FGF-5, growth hormone, NGF, NT-3, NT-4, NT-5, and NT-6, and most preferably, FGF-5 and thrombopoietin.

The expression "control sequences" refers to DNA sequences necessary for the expression of an operably linked coding sequence in a particular host organism. The control sequences that are suitable for prokaryotes include a promoter such as the AP or trp promoter, optionally an operator sequence, and a ribosome-binding site.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

A "nut" site refers to the N-utilization site to which the N protein binds. The term includes both natural nut and manipulations or variations thereof that still work with the N protein by binding thereto to effect mRNA-specific lambda N anti-termination. Examples include lambda nutL, nutR, Box B by itself, Box A and Box B, mutant nut sites, and nut sites from related lambdoid phages. These are described, for example, in Friedman et al., *Genes Dev.*, 4: 2210–2222 (1990); Mogridge et al., *J. Biol. Chem.*, 273: 4143–4148 (1998); Olson et al., *Cell*, 31: 61–70 (1982); Patterson et al., *J. Mol. Biol.*, 236: 217–228 (1994); and Schauer et al., *J. Mol. Biol.*, 194: 679–690 (1987).

A "non-lambda promoter" and "non-lambda" termination sites indicate respectively promoters and termination sites not from lambda phage, for example, not the lambda $P_L$ promoter. Examples of suitable non-lambda promoters herein include, for example, the trp and AP promoters.

B. Modes for Carrying Out the Invention

In one aspect, a vector is provided for producing a polypeptide heterologous to prokaryotic cells, preferably a mammalian polypeptide, and most preferably a human polypeptide. Such vector has at least the following elements: anti-termination nucleic acid that inhibits intragenic transcription termination, RNA encoding the polypeptide, and one or separate non-lambda promoters for the nucleic acid and RNA. In this vector an RNA recognition site for binding the anti-termination protein produced from the nucleic acid is located 5' of the RNA encoding the polypeptide. The vector may further include nucleic acid encoding a GreA or GreB protein along with a promoter for this nucleic acid, which can be lambda or non-lambda.

In another aspect, a process is described for producing a heterologous polypeptide in prokaryotic host cells. In this process the host cells are cultured and the polypeptide is recovered from the cells or cell culture medium. The cells comprise the components of the above-described vector, i.e., anti-termination nucleic acid that inhibits intragenic transcription termination and RNA encoding the polypeptide, with non-lambda promoters for each, wherein an RNA recognition site for binding the anti-termination protein produced from the nucleic acid is located 5' of the RNA encoding the polypeptide. In this process the anti-termination nucleic acid is expressed at the time of expression of the RNA.

In another embodiment, a vector is set forth that includes nucleic acid encoding GreA or GreB protein and nucleic acid encoding a heterologous polypeptide, along with one or more promoters therefor, which may be lambda or non-lambda promoters.

In a still further embodiment, a process for producing a heterologous polypeptide in prokaryotic host cells is provided involving culturing the host cells, which comprise the components of the above-described GreA/GreB vector, i.e., nucleic acid encoding GreA or GreB protein and nucleic acid encoding the heterologous polypeptide, and one or more promoters for the nucleic acids. After the culturing step, the heterologous polypeptide is recovered from the cells or from the cell culture medium.

The anti-termination system may be performed with or without the presence of nucleic acid encoding GreA or GreB, since by itself the anti-termination system described above results in a significant decrease in heterologous protein truncation and 10Sa tagging and leads to a corresponding increase in full-length protein. The co-expression with GreA or GreB nucleic acid leads to more recombinant protein production, regardless of whether the anti-termination system described herein is used.

The anti-termination nucleic acid as well as the GreA/GreB nucleic acid and the nucleic acid encoding the heterologous protein may be cDNA or genomic DNA from any source. The anti-termination and GreA/GreB nucleic acids are generally the native sequence, but need not be if they provide the same benefits to heterologous polypeptide production as set forth herein.

If the anti-termination factors or GreA or GreB proteins are native products of the host cell, and if the factors controlling expression of these native genes are understood, such factors can be manipulated to achieve over-expression of these genes, e.g., by induction of transcription from the natural promoter using known inducer molecules, by mutation of the nucleic acids controlling or repressing expression of the gene product to produce a mutant strain that inductively over-expresses the gene product, by second site mutations which depress the synthesis or function of factors that normally repress the transcription of the gene product, and the like.

The heterologous nucleic acid (e.g., cDNA or genomic DNA) is suitably inserted into a replicable vector for expression in the prokaryotic cells under the control of a suitable promoter for prokaryotic cells. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for prokaryotic cell transformation generally include, but are not limited to, one or more of the following: a signal sequence, an origin of replication, one or more marker genes, and a promoter.

The promoters herein may be constitutive or inducible, preferably inducible, and are recognized by the host prokaryotic organism and operably linked to the GreA/GreB-, and/or anti-termination-, and polypeptide-encoding nucleic acid components of the vectors herein. For the anti-termination plasmid, the promoter is non-lambda. For the plasmid that does not contain anti-termination nucleic acid, the promoter may be lambda or non-lambda. The vectors herein contain either one promoter for all two or three elements, provided it is appropriate for all the elements, or two or more separate promoters, which may be the same or different provided they are appropriate, operably linked to each of the nucleic acids encoding the anti-termination factor, the polypeptide, and/or GreA/GreB protein. The promoters are selected to be compatible with the cell type in which expression is to be performed.

For the anti-termination factor the promoter is non-lambda, and for the GreA/GreB the promoter may be lambda or non-lambda. Suitable non-lambda promoters for use in the preferred cell type, *E. coli*, include, for example, the β-lactamase and lactose (lac) promoter systems (Chang et al., *Nature*, 275: 615 (1978); Goeddel et al., *Nature*, 281: 544 (1979)), the arabinose promoter system (Guzman et al., *J. Bacteriol.*, 174: 7716–7728 (1992)), AP, a trp promoter system (Goeddel, *Nucleic Acids Res.*, 8: 4057 (1980) and EP 36,776), hybrid promoters such as the tac promoter (deBoer et al., *Proc. Natl. Acad. Sci. USA*, 80: 21–25 (1983)), and the T3 or T7 promoter (See generally, e.g., Itakura et al., *Science*, 198: 1056–1063 (1977); Goeddel et al., *Proc. Natl. Acad. Sci. USA*, 76: 106–110 (1979), Emtage et al., *Nature*, 283: 171–174 (1980); and Martial et al., *Science*, 205: 602–606 (1979)). The most preferred non-lambda promoters herein are the trp and AP promoters.

Suitable lambda or non-lambda promoters for use with prokaryotic hosts include the non-lambda promoters set forth above, plus the lambda promoters, i.e., those from lambda phage, for example, the lambda $P_L$ promoter and the lambda $P_r$ promoter. However, other known lambda and non-lambda promoters are suitable. Their nucleotide sequences have been published, thereby enabling a skilled worker operably to ligate them to DNA encoding the polypeptide of interest or to the anti-termination or GreA or GreB genes (Siebenlist et al., *Cell*, 20: 269 (1980)) using linkers or adaptors to supply any required restriction sites.

Promoters for use in prokaryotic systems also generally contain a Shine-Dalgarno (SD) sequence operably linked to the DNA encoding the polypeptide of interest. The promoter can be removed from the prokaryotic source DNA by restriction enzyme digestion and inserted into the vector containing the desired DNA.

If the host contains a psts variant gene, the expression vector for producing a heterologous polypeptide suitably contains an AP promoter that is recognized by the host organism and is operably linked to the nucleic acid encoding the polypeptide of interest. This promoter initiates increased levels of transcription from DNA under its control in response to a decreased concentration of inorganic phosphate in the culture medium. The AP promoter can be removed from the prokaryotic source DNA by restriction enzyme digestion and inserted into the vector containing the desired DNA.

In one alternative, the prokaryotic cells comprise two separate vectors respectively containing the anti-termination nucleic acid and/or GreA/GreB protein and the RNA encoding the heterologous polypeptide.

In another alternative, the anti-termination or greA/greB nucleic acid and the RNA encoding the heterologous polypeptide are contained on the same vector and are under the control of a single promoter or more than one separate inducible promoters. In this case, the polypeptide may be suitably fused in-frame to an anti-terminator protein and/or GreA or GreB protein as defined above such that the combined coding sequence is operably linked to a single promoter. Hence, the polypeptide gene and the anti-termination nucleic acid and/or greA/greB nucleic acid are suitably coupled to form a polycistronic unit. Alternatively, they may be independently expressed under separate, differently inducible promoters on the same vector so that initiation of expression can occur in the proper order.

The anti-termination and/or greA/greB nucleic acid and polypeptide nucleic acid can be anywhere in the cell cytoplasm, including the chromosome. Hence, they may be integrated into the host cell genome or contained on autonomously replicating plasmids. The anti-termination nucleic acid such as the N or Q gene can be expressed with any reasonably controlled promoter, and is preferably only expressed when the polypeptide RNA is turned on.

The vectors herein that contain the anti-termination nucleic acid also contain a RNA recognition site. This would include the Box B sequence in NutR or NutL for phage λN protein. This may also include a Box A site if the anti-termination factor is a phage protein. The RNA recognition site is engineered on the polypeptide mRNA at the 5' end. The anti-termination nucleic acid then binds to its RNA recognition site on the polypeptide mRNA and, in conjunction with RNA polymerase and several host factors such as nus factors, in the case of the N gene, forms an anti-termination complex.

Preferably the Nut site is a NutR site, more preferably a λ NutR site, more preferably a complete BoxA and BoxB NutR or a partial BoxB. The complete sequences of Nut sites, which include Box A and Box B domains from phages λ, φ21, and P22, have been published (Lazinski, *Cell*, 59: 207–218 (1989)). Box B is responsible for binding an anti-terminator protein. Box A sequences exist not only in phages, but in a variety of other anti-termination operons, including the ribosomal RNA operons of *E. coli* (Friedman and Olson, *Cell*, 34: 143–149 (1983); Li et al., *Cell*, 38: 851–860 (1984)). A conserved sequence of 8–12 nucleotides proximal to the promoter in a natural operon, Box A is responsible for binding a host elongation factor that interacts with the anti-termination protein to stimulate anti-termination activity (Greenblatt et al., *Nature*, 364: 401–406 (1993)).

The Box A domain should preferably match the anti-terminator protein encoded by the gene used. Thus, if the anti-terminator protein is the phage λN protein, one may choose a λ, NutL, or NutR Box A sequence, which differ slightly in nucleotide sequence. Analogously, if the anti-termination protein is a phage P22 N protein, one may choose a P22 Nut Box A sequence.

The source of the λN protein is one that is suitable, including from the coding region of the N protein gene of pHE6 (Franklin and Bennett, *Gene*, 8: 107–119 (1979); EP 467,676 published Jan. 22, 1992) that is removed at the 7 HinfI restriction site. Alternatively, one can use the commercially available plasmid from Pharmacia LKB or a plasmid disclosed in EP 700,997, for example.

In general, plasmid vectors containing replicon and control sequences that are derived from species compatible with the host cell are used in connection with prokaryotic hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 (1977)). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

The DNA encoding the polypeptide of interest herein may be expressed not only directly, but also as a fusion with another polypeptide, preferably a signal (leader) sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For, e.g., prokaryotic host cells that do not recognize and process the native polypeptide signal sequence, the signal sequence is substituted by a prokaryotic signal sequence selected, for example, from the group consisting of the alkaline phosphatase, penicillinase, lpp, or heat-stable enterotoxin II leader sequences.

The vector also contains a transcription termination site. The choice of termination site is usually not critical. Termination sites are RNA sequences of about 50–100 bases downstream from the translational stop site of a protein-coding sequence. Frequently, RNA termination sites can fold to a hairpin structure. Termination sites are recognized by RNA polymerase as a signal to cease transcription (von Hippel, *Science*, 255: 809 (1992)). In eukaryotic cells, the selection of termination site depends on the promoter to which the genes are linked. However, in prokaryotic cells, RNA polymerase recognizes virtually any prokaryotic termination site, so the choice of termination site is not critical. In some vectors, multiple termination sites are included in tandem.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of prokaryotes. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. One example of a selection scheme utilizes a drug to arrest growth of a host cell. Those cells that are successfully transformed with a heterologous gene produce a protein conferring drug resistance and thus survive the selection regimen.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA,* 74: 5463–5467 (1977), Messing et al., *Nucleic Acids Res.,* 9: 309 (1981), or Maxam et al., *Methods in Enzymology,* 65: 499 (1980).

Suitable prokaryotic cells useful as host cells herein include bacteria, for example, archaebacteria and eubacteria, especially eubacteria, and most preferably Enterobacteriaceae. Examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla,* and *Paracoccus*. These host cells may be lysogenic. Suitable *E. coli* hosts include *E. coli* W3110 (ATCC 27,325), *E. coli* 294 (ATCC 31,446), *E. coli* B, *E. coli* X1776 (ATCC 31,537), and *E. coli* JM105 (New England Biolabs). These examples are illustrative rather than limiting. Mutant cells of any of the above-mentioned prokaryotic cells may also be employed. It is, of course, necessary to select the appropriate prokaryotic cells taking into consideration replicability of the replicon in the cells of a prokaryote. For example, *E. coli, Serratia,* or *Salmonella* species can be suitably used as the host when well-known plasmids such as pBR322, pBR325, pACYC177, or pKN410 are used to supply the replicon.

*E. coli* strain W3110 is a preferred host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 1A2, which has the complete genotype tonA$\Delta$ (also known as $\Delta$fhuA); *E. coli* W3110 strain 9E4, which has the complete genotype tonA$\Delta$ ptr3; *E. coli* W3110 strain 27C7 (ATCC 55,244), which has the complete genotype tonA$\Delta$ ptr3 phoA$\Delta$SE15 $\Delta$(argF-lac)169 ompT$\Delta$ degP41kan$^r$; *E. coli* W3110 strain 37D6, which has the complete genotype tonA$\Delta$ ptr3 phoA$\Delta$E15 $\Delta$(argF-lac)169 ompT$\Delta$ degP41kan$^r$ rbs7$\Delta$ ilvG; *E. coli* W3110 strain 40B4, which is strain 37D6 with a non-kanamycin-resistant degP deletion mutation; *E. coli* W3110 strain 33D3, which has the complete genotype tonA ptr3 lacIq LacL8 ompT degP kan$^r$; *E. coli* W3110 strain 36F8, which has the complete genotype tonA phoA $\Delta$(argF-lac) ptr3 degp kan$^R$ ilvG+, and is temperature resistant at 37° C.; an *E. coli* strain having the mutant periplasmic protease(s) disclosed in U.S. Pat. No. 4,946,783 issued Aug. 7, 1990; *E. coli* W3110 strain 52A7, which has the complete genotype tonA$\Delta$ (fhuA$\Delta$) lon$\Delta$ gale rpohts (htpRts) $\Delta$clpP lacIq; *E. coli* W3110 strain 54C2, which has the complete genotype fhuA (tonA) lon galE rpoHts (htpRts) clpp lacIg; and *E. coli* W3110 strain 59B9, which has the complete genotype fhuA$\Delta$(tonA$\Delta$)lon$\Delta$ galE rpoHts (htpRts) $\Delta$clpP lacIq $\Delta$ompT $\Delta$(nmpc-fepE) $\Delta$lacY.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* (New York: Cold Spring Harbor Laboratory Press, 1989), is generally used for prokaryotic cells that contain substantial cell-wall barriers. Another method for transformation employs polyethylene glycol/DMSO, as described in Chung and Miller, *Nucleic Acids Res.,* 16: 3580 (1988). Yet another method is the use of the technique termed electroporation.

Host cells are transformed with the above-described expression vectors of this invention and cultured in conventional nutrient media modified as appropriate if promoters are induced. Suitable media for this purpose are described generally, e.g., in Sambrook et al., supra. Any other necessary supplements may also be included at appropriate concentrations introduced alone or as a mixture with another supplement or medium such as a complex nitrogen source. The pH of the medium may be any pH from about 5–9, depending mainly on the host organism.

Gene expression may be measured in a sample by any means, including indirectly or directly, for example, by conventional northern blotting to quantitate the transcription of mRNA (Thomas, *Proc. Natl. Acad. Sci. USA,* 77: 5201–5205 (1980)). Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

Procedures for observing whether an expressed or over-expressed gene product is secreted are readily available to the skilled practitioner. Once the culture medium is separated from the host cells, for example, by centrifugation or filtration, the gene product can then be detected in the cell-free culture medium or cell culture by taking advantage of known properties characteristic of the gene product. Such properties can include the distinct immunological, enzymatic, or physical properties of the gene product.

For example, if an over-expressed gene product has a unique enzyme activity, an assay for that activity can be performed on the culture medium used by the host cells or extracted cell pellets. Moreover, when antibodies reactive against a given gene product are available, such antibodies can be used to detect the gene product in any known immunological assay (e.g., as in Harlowe et al., *Antibodies: A Laboratory Manual* (Cold Spring Harbor Laboratory Press: New York, 1988)).

If the gene product is secreted, it can also be detected using tests that distinguish polypeptides on the basis of characteristic physical properties such as molecular weight. To detect the physical properties of the gene product, all polypeptides newly synthesized by the host cell can be labeled, e.g., with a radioisotope. Common radioisotopes that can be used to label polypeptides synthesized within a host cell include tritium ($^3$H), carbon-14 ($^{14}$C), sulfur-35 ($^{35}$S), and the like. For example, the host cell can be grown in $^{35}$S-methionine or $^{35}$S-cysteine medium, and a significant amount of the $^{35}$S label will be preferentially incorporated into any newly synthesized polypeptide, including the over-expressed heterologous polypeptide. The $^{35}$S-containing culture medium is then removed and the cells are washed and placed in fresh non-radioactive culture medium. After the cells are maintained in the fresh medium for a time and under conditions sufficient to allow secretion of the $^{35}$S-radiolabeled, expressed heterologous polypeptide, the culture medium is collected and separated from the host cells. The molecular weight of the secreted, labeled polypeptide in the culture medium or cell-associated in the cell pellet can then be determined by known procedures, e.g., polyacrylamide gel electrophoresis. Such procedures, and/or other procedures for detecting secreted gene products, are provided, for example, in Goeddel, D. V. (ed.) 1990, Gene Expression Technology, *Methods in Enzymology,* Vol. 185 (Academic Press), and Sambrook et al., supra.

For secretion of an expressed or over-expressed gene product, the host cell is cultured under conditions sufficient for secretion of the gene product. Such conditions include, e.g., temperature, nutrient, and cell-density conditions that permit secretion by the cell. Moreover, such conditions are those under which the cell can perform basic cellular functions of transcription, translation, and passage of proteins from one cellular compartment to another, as are known to those skilled in the art.

If the secretory elements are in place, the polypeptide of interest is recovered from the periplasm or culture medium as a secreted polypeptide. It is often preferred to purify the polypeptide of interest from recombinant cell proteins or polypeptides and from the anti-termination factor or GreA or GreB protein to obtain preparations that are substantially homogeneous as to the polypeptide of interest. As a first step, the culture medium or lysate may be centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane-bound, is soluble, or is present in an aggregated form. The polypeptide thereafter is solubilized and refolded, if necessary, and is purified from contaminant soluble proteins and polypeptides.

One method for isolating exogenous polypeptides from a complex biological mixture containing polypeptides and non-polypeptides contained in a fermentation broth involves contact of reagents with the cells, preferably the cell culture, containing the polypeptide in a non-native conformation, so that an aqueous extraction/isolation can take place. Preferably, the method entails direct addition of reagents to the fermentation vessel after the polypeptide has been produced recombinantly, thereby avoiding extra steps of harvesting, homogenization, and centrifugation to obtain the polypeptide. While the remaining particulates can be removed by Gaulin homogenization and re-suspension, filtration, or a combination thereof, this method utilizes a multiple-phase extraction system for purifying recombinant polypeptides from the remaining particulates.

The following procedures are exemplary of suitable purification procedures: fractionation on immunoaffinity or ion-exchange columns; ethanol precipitation; reverse-phase HPLC; chromatography on silica or on an anion-exchange resin such as DEAE; chromatofocusing; SDS-PAGE; ammonium-sulfate precipitation; and gel filtration using, for example, SEPHADEX™ G-75 medium from Amersham Biosciences.

The invention will be more fully understood by reference to the following examples. They should not, however, be construed as limiting the scope of the invention. All literature and patent citations mentioned herein are expressly incorporated by reference.

EXAMPLE 1

Effect of λN Anti-Termination System on TPO Production (Shake-Flask)

Materials and Methods:

Description and Construction of *E. coli* Expression Vectors

The plasmids pMP331, pMP843, pMP871, pMP931, pMP951, pMP982, pMP945, pMP1016, pMP1086, pMP1099, pMP1201, and pMP1217 are all designed to express full-length mature TPO (deSauvage et al., *Nature,* 369: 533–538 (1994)) in the *E. coli* cytoplasm using a pBR322-based vector (Bolivar et al., *Gene,* 2: 95–113 (1977)). The 332-amino-acid TPO coding sequence is preceded in all plasmids by a leader consisting of the first seven amino acids of the heat-stable enterotoxin II signal sequence (Picken et al., *Infect. Immun.,* 42: 269–275(1983)), followed by eight histidine residues, and finally the thrombin cleavage site IEPR (SEQ ID NO:6). Transcription in the plasmids pMP331, pMP843, pMP871, pMP931, pMP945, pMP951, pMP982, and pMP1217 is under the control of the trp promoter (Yanofsky et al., *Nucleic Acids Res.,* 9: 6647–6668 (1981)), while pMP1016, pMP1086, pMP1099, and pMP1201 use the AP promoter (Kikuchi et al., *Nucleic Acids Res.,* 9: 5671–5678 (1981)). Just downstream of the TPO coding sequence is situated the λt$_o$ transcriptional terminator (Scholtissek et al., *Nucleic Acids Res.,* 15: 3185 (1987)).

Additional genetic elements on pMP843, pMP871, pMP931, and pMP945 include the partial λ nutR site Box B (or B box), while plasmids pMP951, pMP982, pMP1086, pMP1201, and pMP1217 have the complete λ nutR site of Boxes A and B (Olson et al., *Cell,* 31: 61–70 (1982)) at the site where the TPO-encoding message begins. Plasmids pMP871, pMP931, pMP945, pMP951, pMP982, pMP1086, pMP1201, and pMP1217 also contain the gene for λN protein (Franklin, *J. Mol. Biol.,* 181: 75–84 (1984)). Finally, plasmids pMP982, pMP1086, pMP1099, and pMP1201 contain the sequence for a rare arginine tRNA, the argu gene (dnay gene) (Garcia et al., *Cell,* 45: 453–459 (1986)).

The plasmid pDR1 is designed to express the protein GreB (Borukhov et al., *Cell,* supra) under the control of the tacII promoter (DeBoer et al., supra). The backbone of this plasmid is pACYC177 (Chang et al., *J. Bacteriol.,* 134: 1141–1156 (1978); Rose, *Nucleic Acids Res.,* 16: 356

(1988)), which allows it to be compatibly maintained in the same *E. coli* cell with the pBR322-based plasmids.

Plasmid pMP331

The plasmid pMP331 is a derivative of the TPO expression plasmid pMP202 (WO 95/18858 published Jul. 13, 1995). Briefly, pMP202 is designed to express the first 155 amino acids of TPO downstream of a leader comprising seven amino acids of the STII signal sequence, eight histidines, and a thrombin cleavage site. The plasmid pMP331 extends the TPO coding sequence from 155 to 332 amino acids.

Three DNA fragments were ligated together to make pMP331 as shown in FIG. 1, the first of which was the large fragment of the vector pdh108 previously cut with XbaI and StuI. pdh108 is derived from the vector pHGH207-1 (DeBoer et al., *Promoters: Structure and Function* (Praeger: New York, 1982), pp. 462–481) and contains the $\lambda t_o$ transcriptional terminator downstream of the trp promoter. The second part was the 431-base-pair XbaI-BamHI fragment from the plasmid pMP202 encoding the first 122 amino acids of TPO. The third part was an approximately 669-base-pair BamHI-RsaI fragment from phmpII (deSauvage et al., *Nature*, 369: 533–538 (1994)) encoding the last half of the TPO gene product.

Plasmid pMP843

Figure 2:
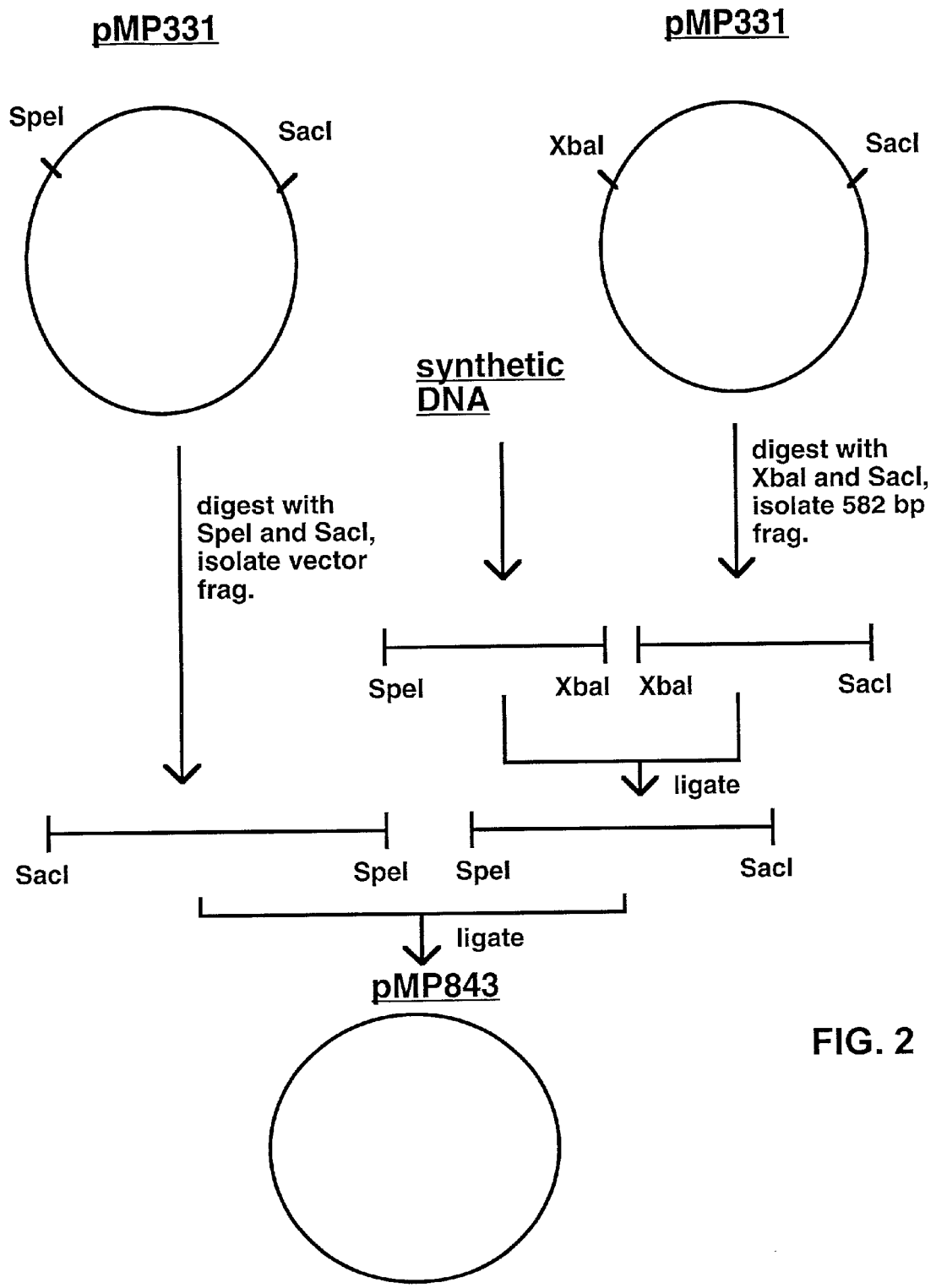
FIG. 2 shows the construction of plasmid pMP843.

The plasmid pMP843 is the result of adding the λ nutB box (nutR Box B) downstream of the trp promoter in plasmid pMP331. Two fragments were ligated together to produce pMP843 as shown in FIG. 2, the first of which was pMP331 in which the small SpeI-SacI fragment had been removed. The second was a 642-base-pair SpeI-SacI fragment obtained by ligating a synthetic DNA duplex to the 582-base-pair XbaI-SacI fragment from pMP331. The synthetic DNA duplex had the following sequence:

```
                    (SEQ ID NOS:7 and 8, respectively)
5'-CTAGTTAACTAGTACGCATTCCAGCCCTGAAAAAGGGCAAAGTTCAC
GTAAAAAGGATATAATTGATCATGCGTAAGGTCGGGACTTTTTCCCGTTT
CAAGTGCATTTTTCCTATAGATC-5'
```

Plasmid pMP871

Figure 3:
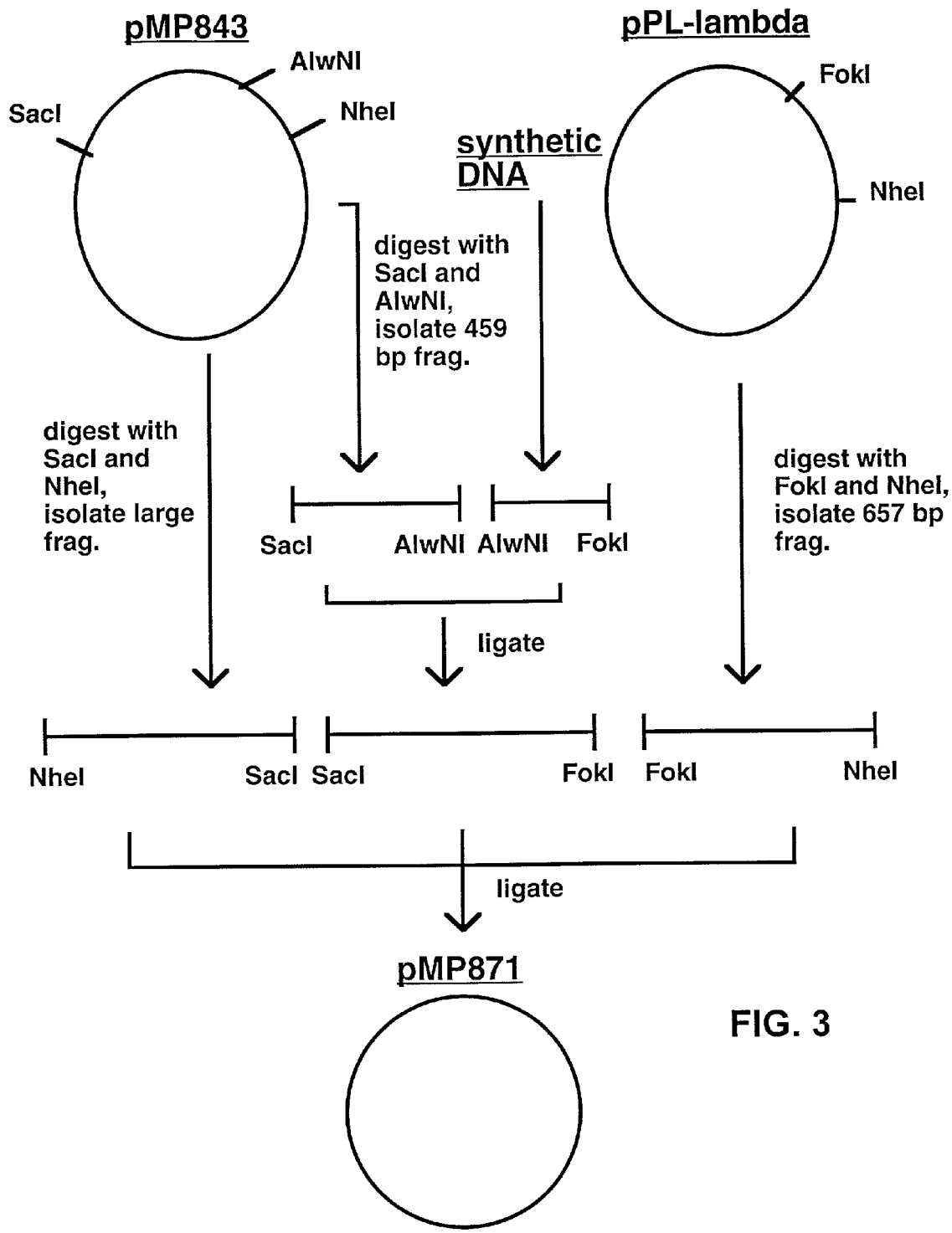
FIG. 3 shows the construction of plasmid pMP871.

The plasmid pMP871 is derived from pMP843 and contains the gene for λN protein polycistronically coupled downstream of the TPO coding sequence. pMP871 was constructed as shown in FIG. 3, by ligating together three DNA fragments, the first of which was the vector pMP843 from which the small SacI-NheI fragment had been removed. The second is an approximately 500-base-pair SacI-FokI fragment prepared by pre-ligating a synthetic DNA duplex to the 459-base-pair SacI-AlwNI fragment from pMP843 encoding amino acids 174–327 of TPO. The synthetic DNA duplex had the following sequence:

```
                        (SEQ ID NOS:9 and 10, respectively)
5'-CTGTCTCAGGAAGGGTAAGCTTTTATGGATGCACAAACACTTAGACA
GAGTCCTTCCCATTCGAAAATACCTACGTGTTTGTGCGGC-5'
```

The final part in the ligation was an approximately 657-base-pair FokI-NheI fragment from the commercial vector pPL-λ (Pharmacia Biotech Inc.) encoding amino acids 7–107 of λN protein.

Plasmid pMP931

Figure 4:
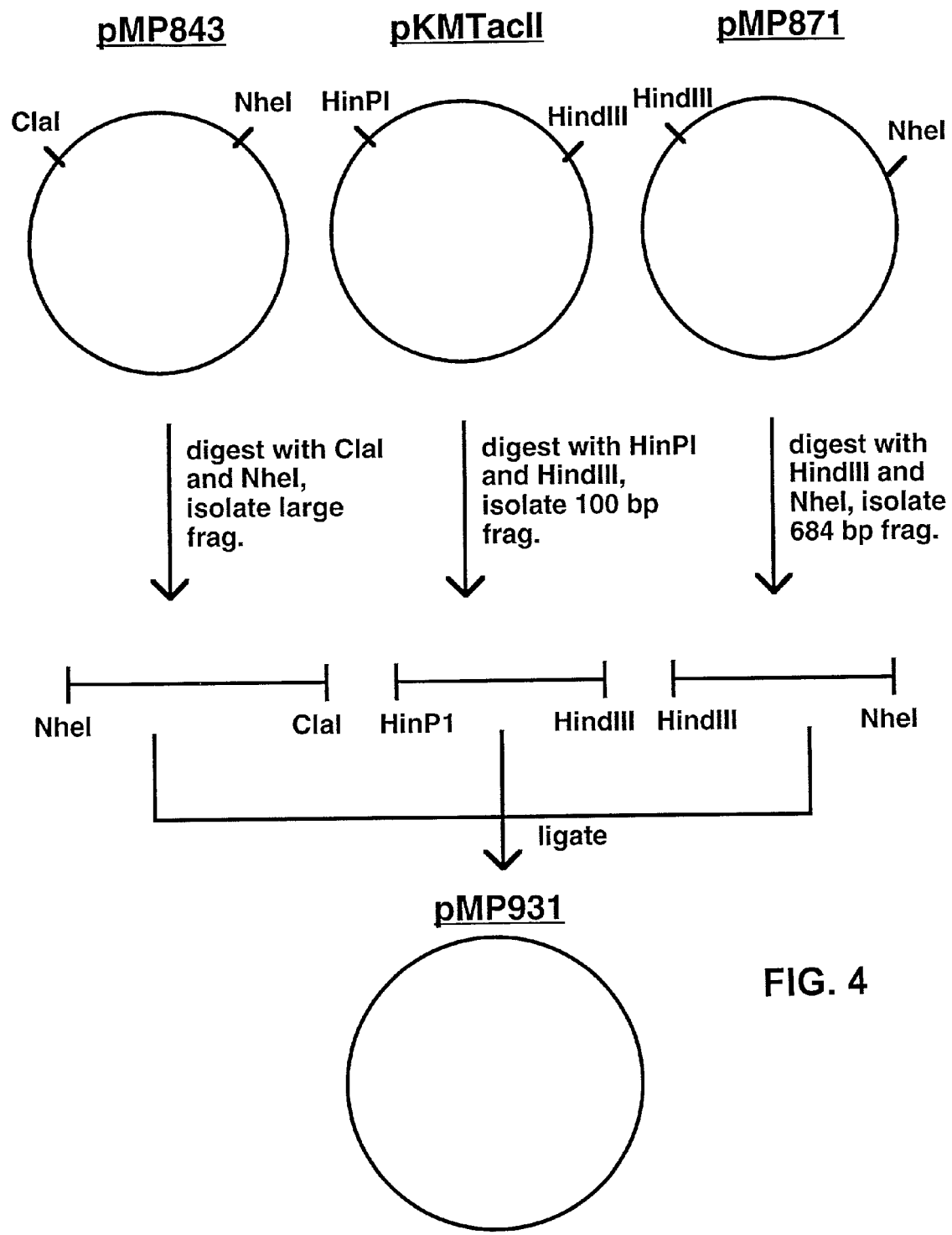
FIG. 4 shows the construction of plasmid pMP931.

The plasmid pMP931 is a derivative of pMP843 in which the λN gene is placed under the control of the tacII promoter. As shown in FIG. 4, pMP931 was constructed by ligating together three DNA fragments. The first of these was the vector pMP843 in which the small ClaI-NheI fragment had been removed. The second was an approximately 100-base-pair HinPI-HindIII fragment from the plasmid pKMTacII (DeBoer et al., (1983), supra) containing the tacII promoter. The third part in the ligation was a 684-base-pair HindIII-NheI fragment from pMP871 encoding the λN gene.

Plasmid pMP945

Figure 5:
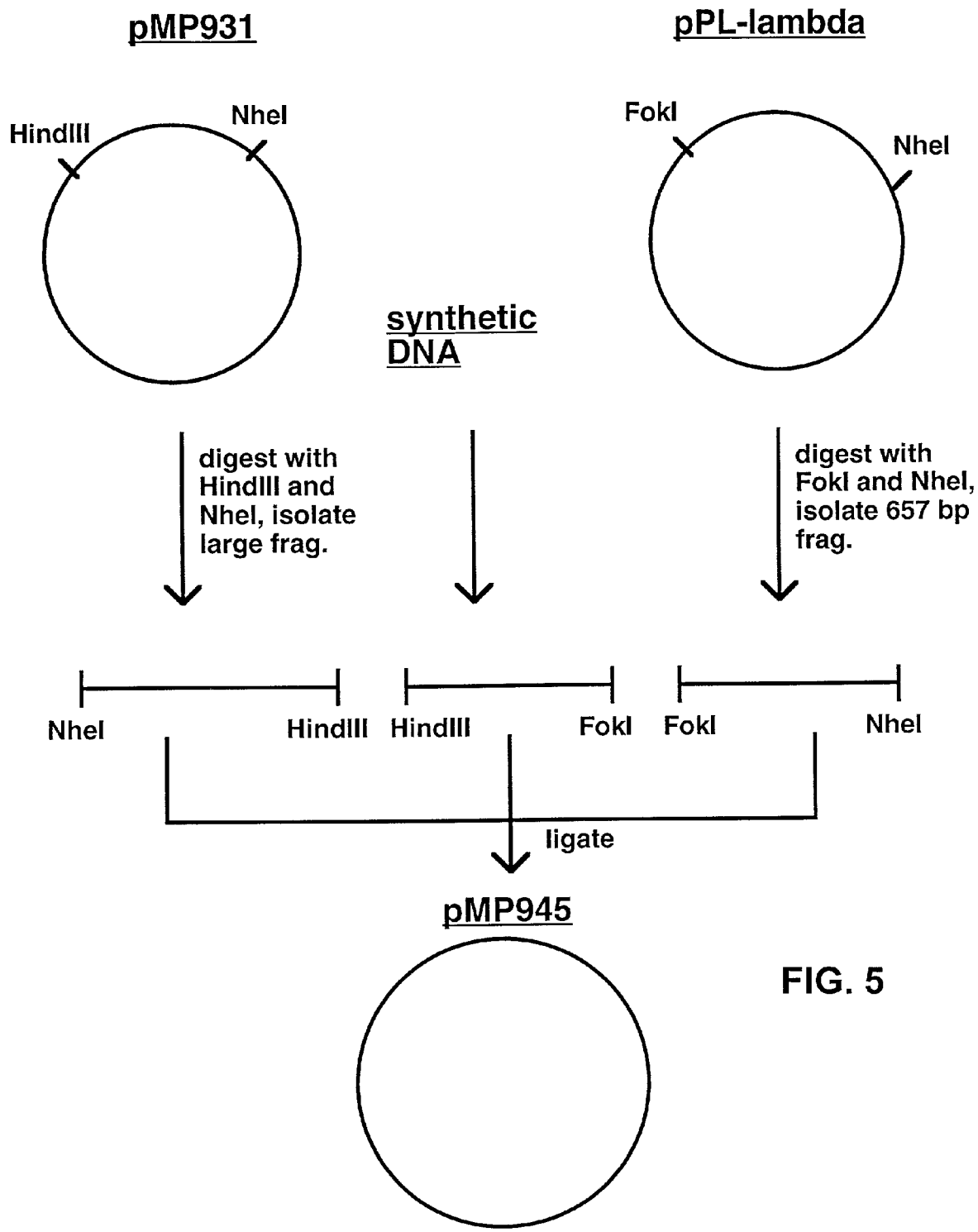
FIG. 5 shows the construction of plasmid pMP945.

The plasmid pMP945 is a derivative of pMP931 in which λN gene expression from the tacII promoter is accompanied by a full Shine-Dalgarno sequence for higher translation levels. As shown in FIG. 5, this plasmid was constructed by ligating together three DNA fragments, the first of which was the large vector fragment obtained by digesting pMP931 with HindIII and NheI. The second fragment was a synthetic DNA duplex with the following sequence:

```
            (SEQ ID NOS:11 and 12, respectively)
5'-AGCTTAGGATTCTAGAATTATGGATGCACAAACAC
   ATCCTAAGATCTTAATACCTACGTGTTTGTGCGGC-5'
```

The last part was the 657-base-pair FokI-NheI fragment used in the construction of pMP871.

Plasmid pMP951

Figure 6:
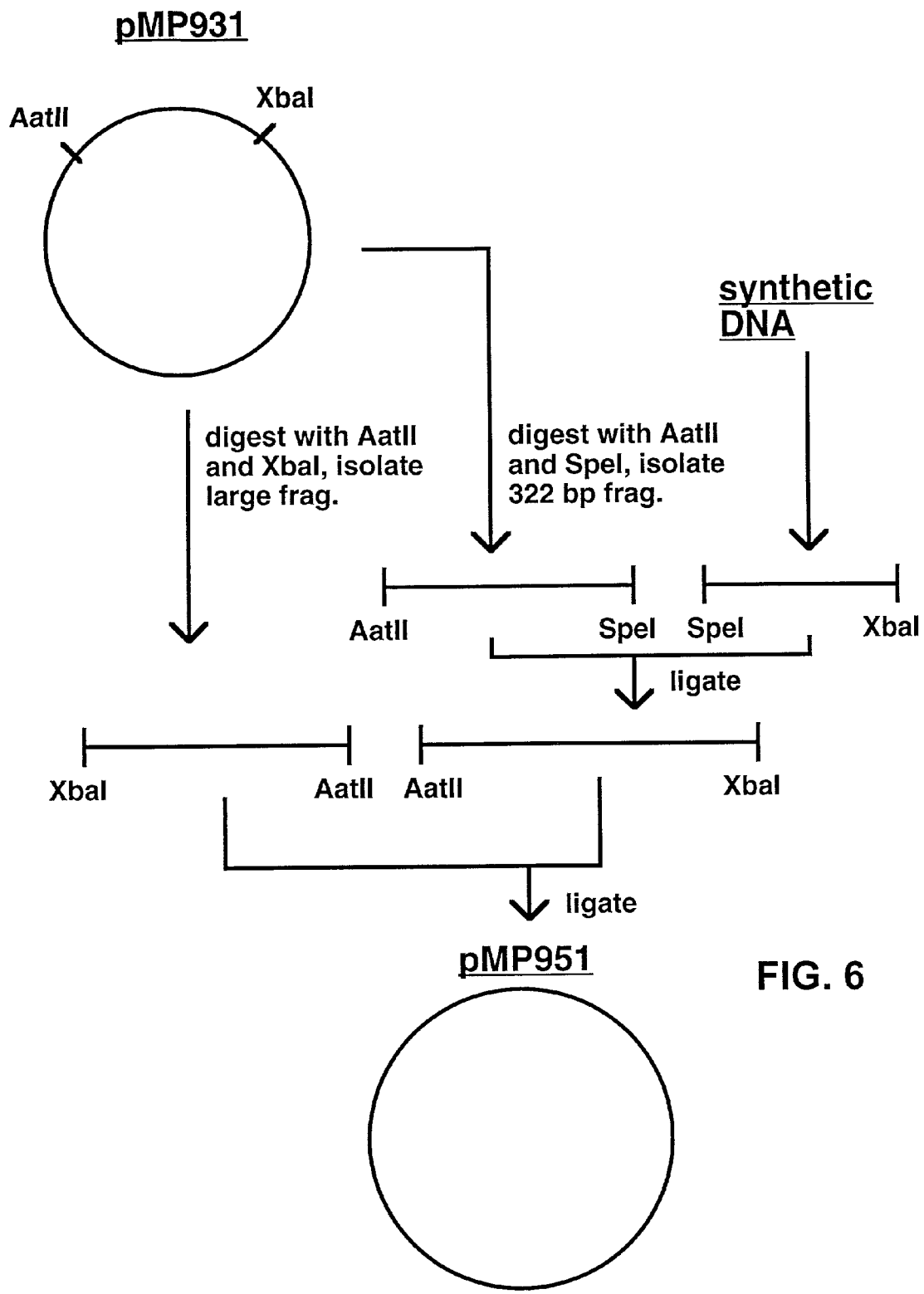
FIG. 6 shows the construction of plasmid pMP951.

The plasmid pMP951 is derived from pMP931 and additionally contains the full nut site (both Boxes A and B). As shown in FIG. 6, pMP951 was constructed by ligating together two DNA fragments. The first of these was the vector pMP931 from which the small AatII-XbaI fragment had been removed. The second was prepared by pre-ligating a synthetic DNA duplex to the 322-base-pair AatII-SpeI fragment from pMP931. The synthetic DNA duplex had the following sequence:

```
                                (SEQ ID NO:13)
5'-CTAGTTAACTAGTACGCAACGCTCTTACACATTCCAGCC- (SEQ ID NO:14)
   AATTGATCATGCGTTGCGAGAATGTGTAAGGTCGG-

-CTGAAAAAGGGCAAAGTTCACGTAAAAAGGATAT

-GACTTTTTCCCGTTTCAAGTGCATTTTTCCTATAGATC-5'
```

Plasmid pMP982

Figure 7:
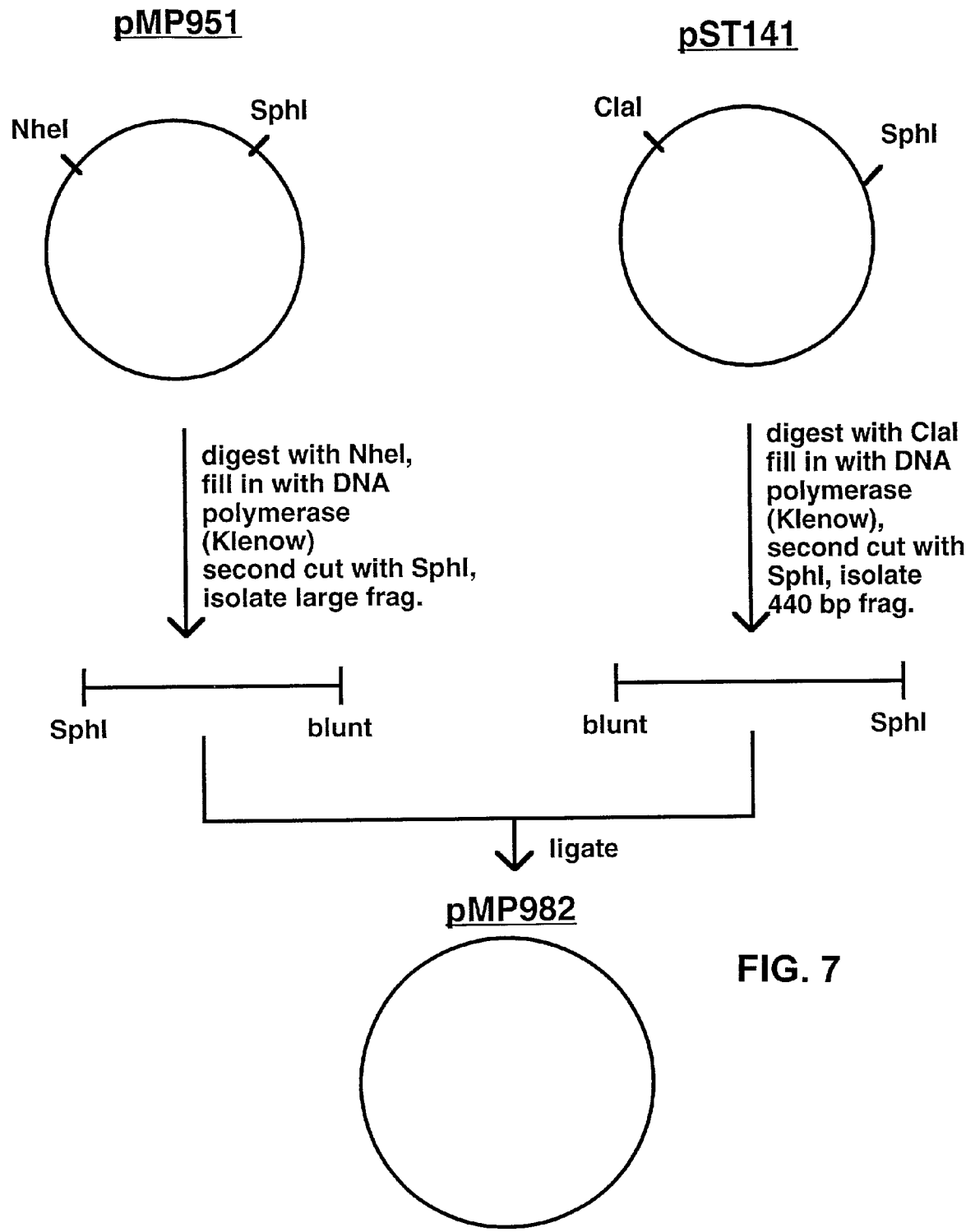
FIG. 7 shows the construction of plasmid pMP982.

The plasmid pMP982 is a derivative of pMP951 with the addition of the argu gene on the plasmid downstream of the λN gene. As shown in FIG. 7, this plasmid was constructed by ligating together two DNA fragments. The first of these was the vector pMP951 in which the small NheI-SphI fragment had been removed, and in which the NheI site had been blunted by treatment with DNA polymerase I (Klenow). The second part was a 440-base-pair ClaI-SphI fragment from pST141 in which the ClaI site had been blunted by treatment with DNA polymerase I (Klenow). pST141 is a derivative of the plasmid pHGH207-1 (DeBoer et al., (1983), supra), and this fragment only encodes the argu gene (Garcia et al., *Cell*, 45: 453–459 (1986)).

Plasmid pMP1016

Figure 8:
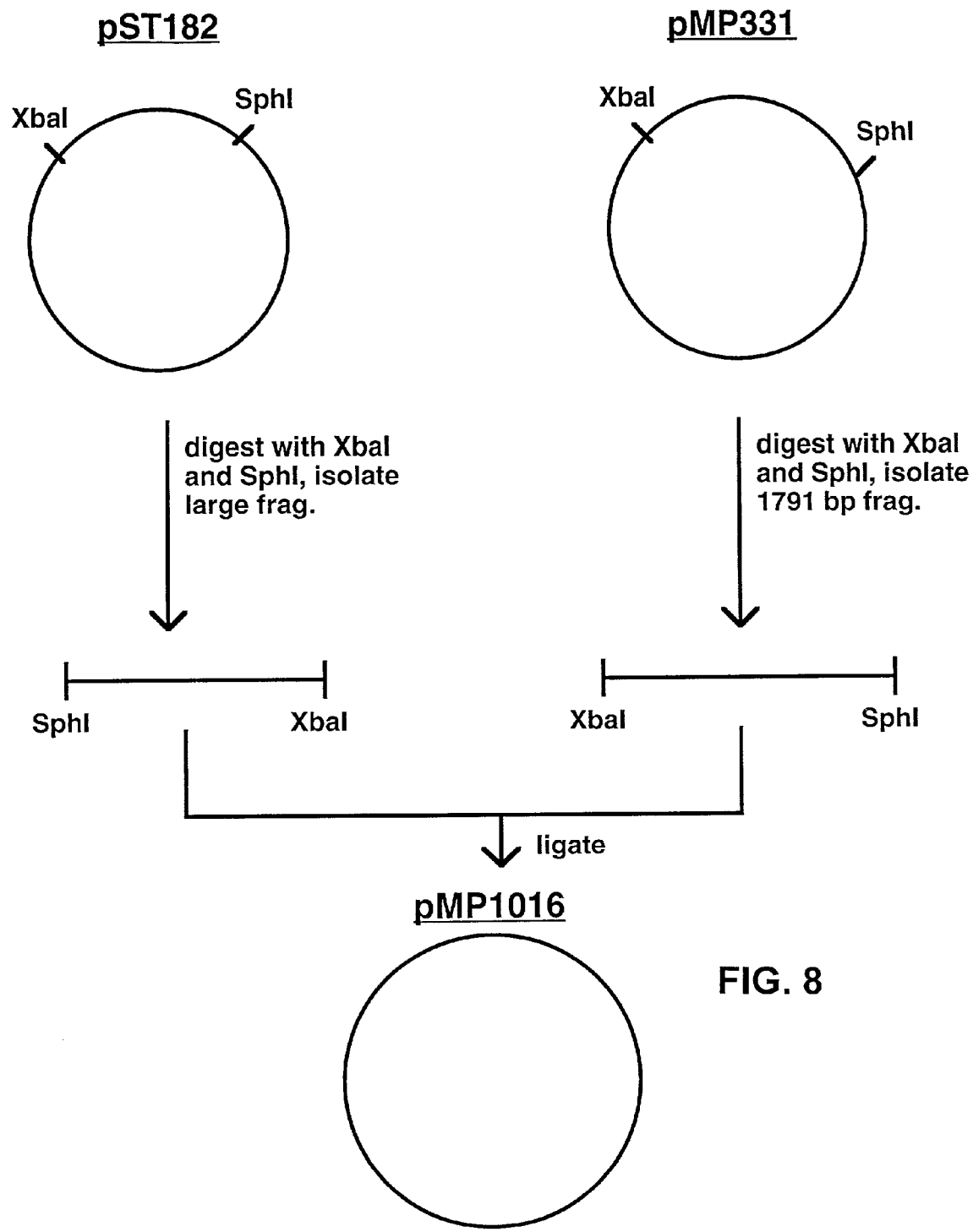
FIG. 8 shows the construction of plasmid pMP1016.

The plasmid pMP1016 is a derivative of pMP331 in which the trp promoter has been replaced with the AP promoter. This plasmid was constructed as shown in FIG. 8 by ligating together two DNA fragments. The first of these was the vector pST182 in which the small XbaI-SphI fragment had been removed. The plasmid pST182 is a derivative of phGH1 (Chang et al., *Gene*, 55: 189–196 (1987)), and this latter vector could be used instead to generate this DNA fragment. The second part in the ligation was a 1791-base-pair XbaI-SphI fragment from pMP331 encoding the TPO gene product and the λt$_o$ transcriptional terminator.

Plasmid pMP1086

Figure 9:
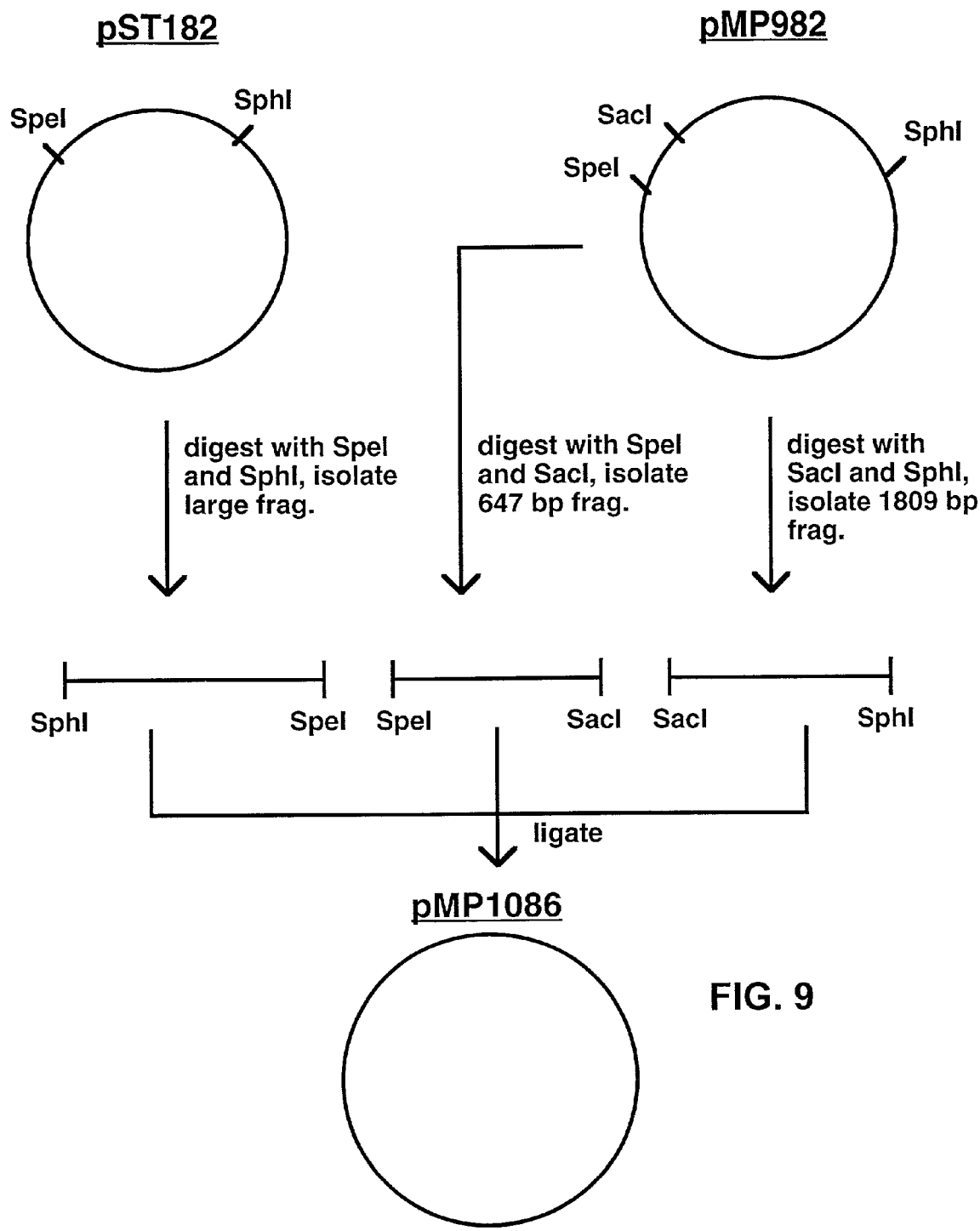
FIG. 9 shows the construction of plasmid pMP1086.

The plasmid pMP1086 is derived from pMP982 and results in the AP promoter being substituted for the trp promoter. Three DNA fragments were ligated together to construct pMP1086 as shown in FIG. 9. The first of these was the vector pST182 from which the small SpeI-SphI fragment had been removed. The plasmid pST182 is a derivative of phGH1 (Chang et al., *Gene*, supra) and this latter vector could be used instead to generate this fragment. The second part in the ligation was a 647-base-pair SpeI-SacI fragment from pMP982 encoding the nut site and the first 173 amino acids of TPO. The third part was a 1809-base-pair SacI-SphI fragment from pMP982 encoding TPO amino acids 174–332, and containing the λt$_o$ terminator, λN gene, and argu gene.

Plasmid pMP1099

Figure 10:
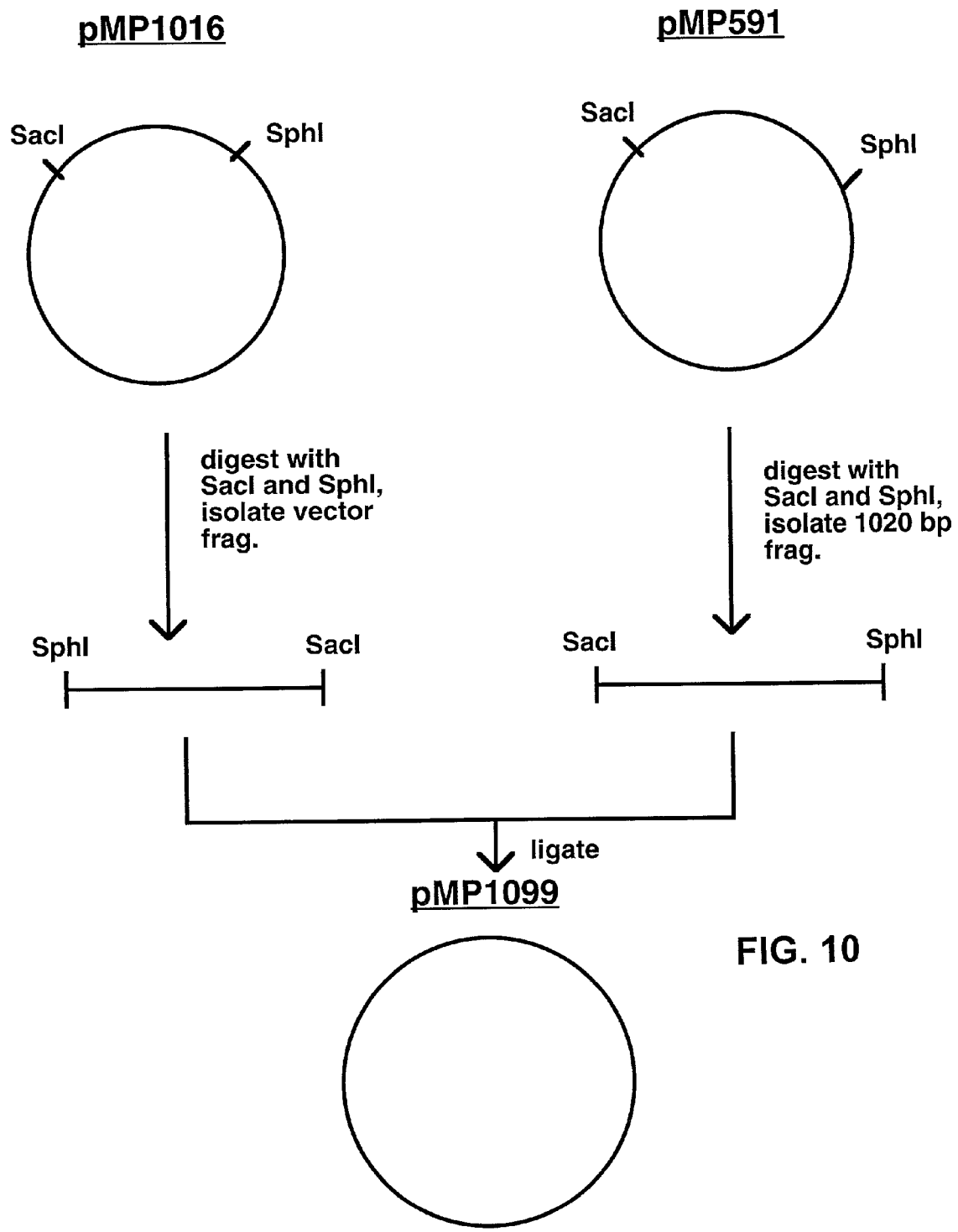
FIG. 10 shows the construction of plasmid pMP1099.

The plasmid pMP1099 is derived from pMP1016 and additionally contains the argu gene downstream of the λt$_o$ transcriptional terminator. As shown in FIG. 10, it was constructed by ligating together two DNA fragments. The first of these was the vector pMP1016 in which the small SacI-SphI fragment had been removed. The second was a 1020-base-pair SacI-SphI fragment from the plasmid pMP591 encoding the last 159 amino acids of TPO, the λt$_o$ transcriptional terminator, and the argu gene. The plasmid pMP591 is a derivative of pMP331 with the addition of the argu gene just downstream of the λt$_o$ transcriptional terminator.

Plasmid pMP1201

Figure 11:
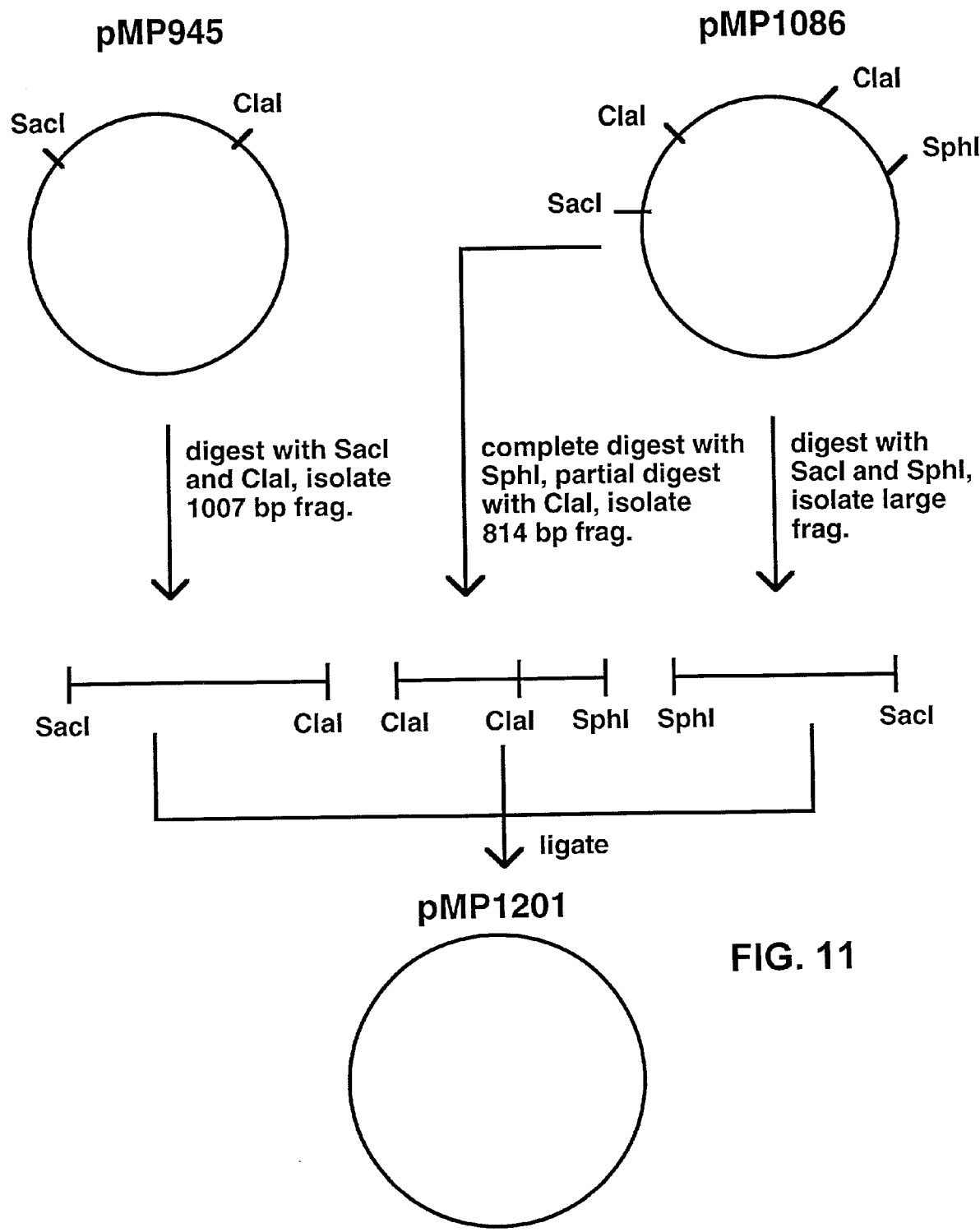
FIG. 11 shows the construction of plasmid pMP1201.

The plasmid pMP1201 is a derivative of pMP1086 in which λN gene expression from the tacII promoter is accompanied by a full Shine-Dalgarno sequence for higher translation levels. As shown in FIG. 11, this plasmid was constructed by ligating together three DNA fragments, the first of which was the large vector fragment obtained by digesting pMP1086 with SacI and SphI. The second was a 1007-base-pair SacI-ClaI fragment from pMP945 containing the tacII promoter with full Shine-Dalgarno and most of the λN gene. The final piece was a 814-base-pair ClaI-SphI fragment obtained by digesting pMP1086 completely with SphI, and partially with ClaI.

Plasmid pMP1217

Figure 12:
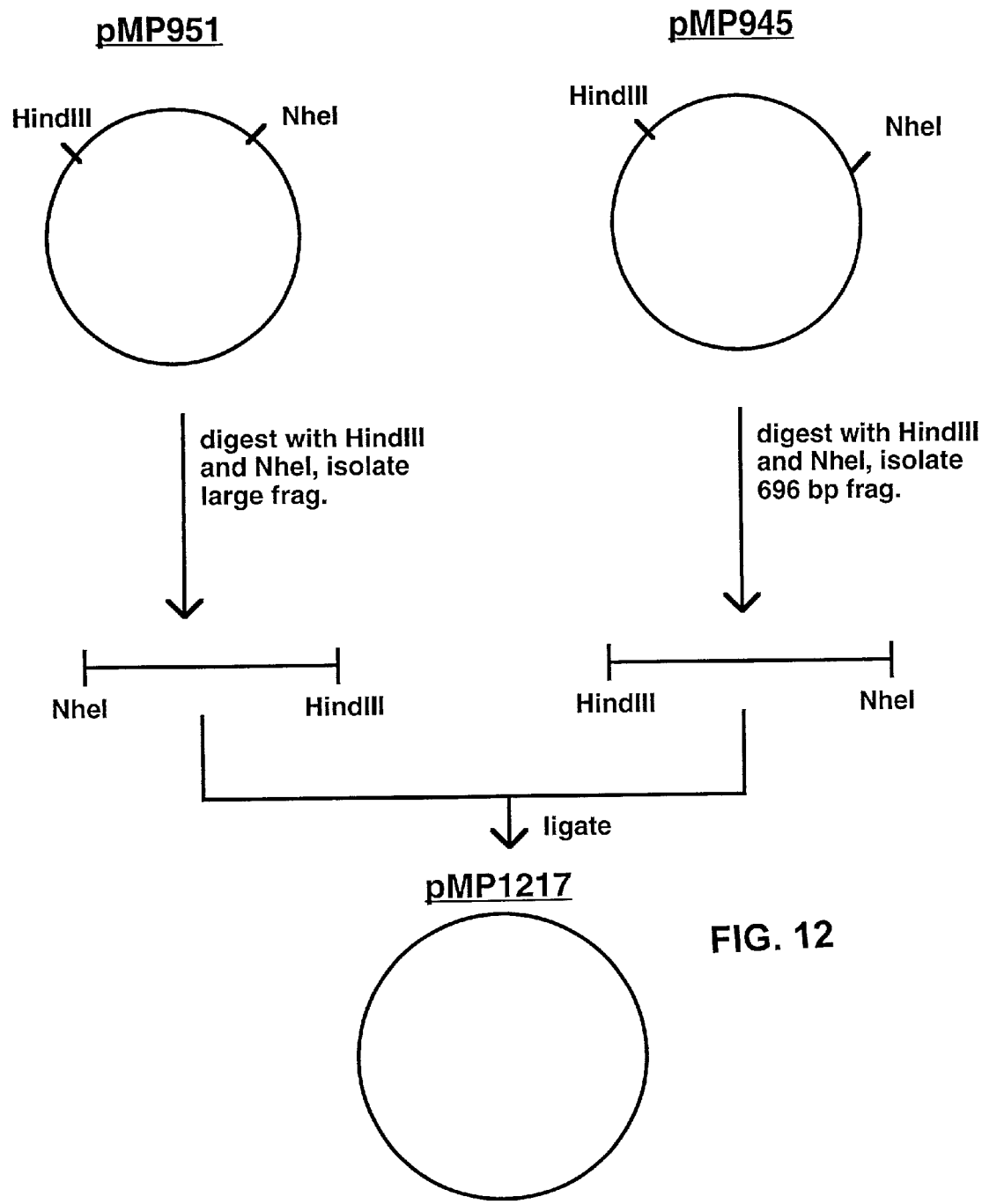
FIG. 12 shows the construction of plasmid pMP1217.

The plasmid pMP1217 is a derivative of pMP951 in which λN gene expression from the tacII promoter is accompanied by a full Shine-Dalgarno sequence for higher translation levels. As shown in FIG. 12, this plasmid was constructed by ligating together two DNA fragments. The first of these was the large vector fragment of pMP951 after digestion with HindIII and NheI. The second was a 696-base-pair HindIII-NheI fragment from pMP945 encoding a full Shine-Dalgarno sequence preceding the λN gene.

Plasmid pJJ142

Figure 13:
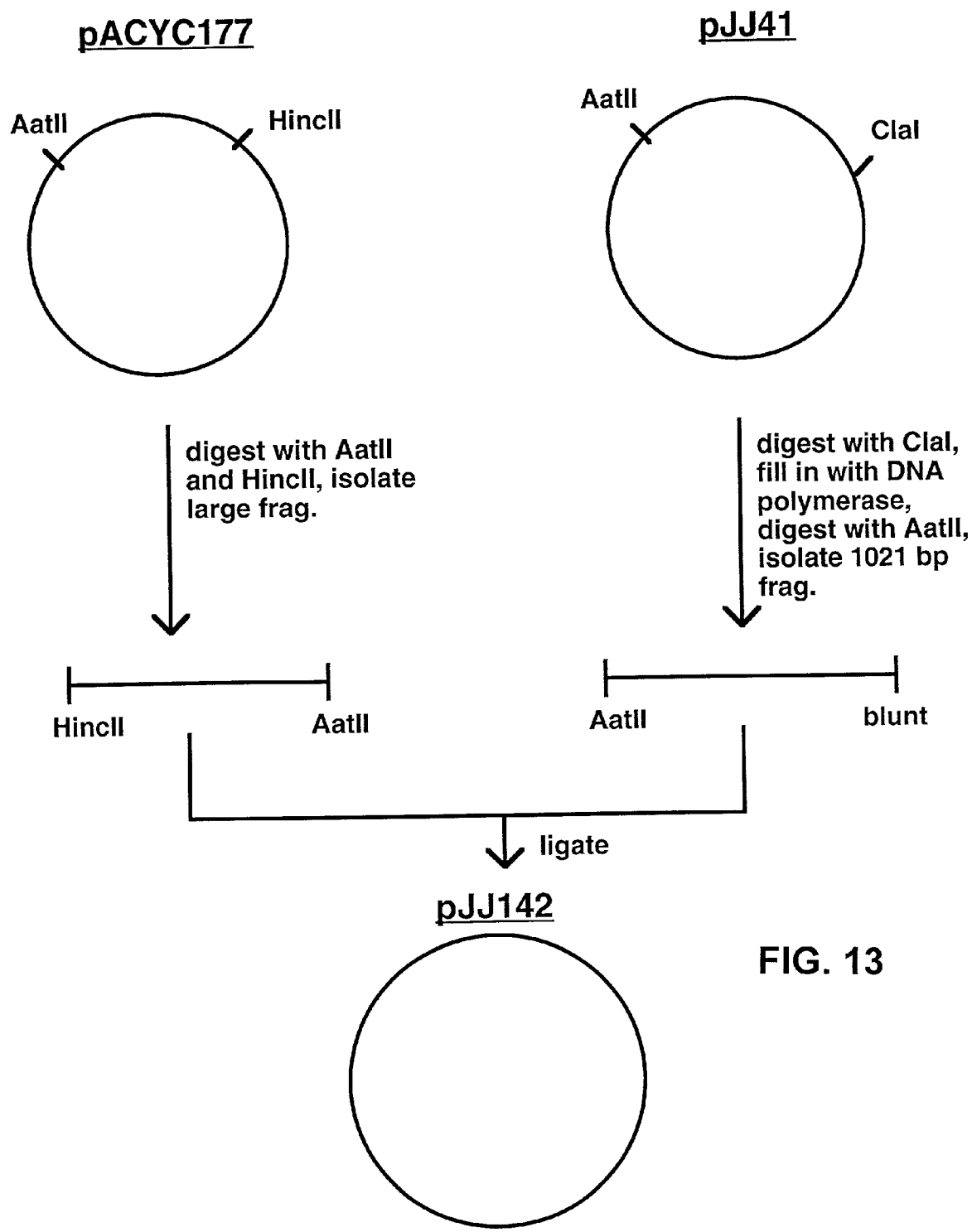
FIG. 13 shows the construction of plasmid pJJ142.

The plasmid pJJ142 is an intermediate in the construction of pDR1 and was prepared by ligating together two DNA fragments as shown in FIG. 13. The first of these was the plasmid pACYC177 in which the small AatII-HincII fragment had been removed. The second part in the ligation was the 1021-base-pair AatII-ClaI fragment from pJJ41 (U.S. Pat. No. 5,639,635) in which the ClaI site had been blunted by treatment with DNA polymerase I (Klenow). This latter fragment encodes the tacII promoter followed by the dsbC gene.

Plasmid pDR1

Figure 14:
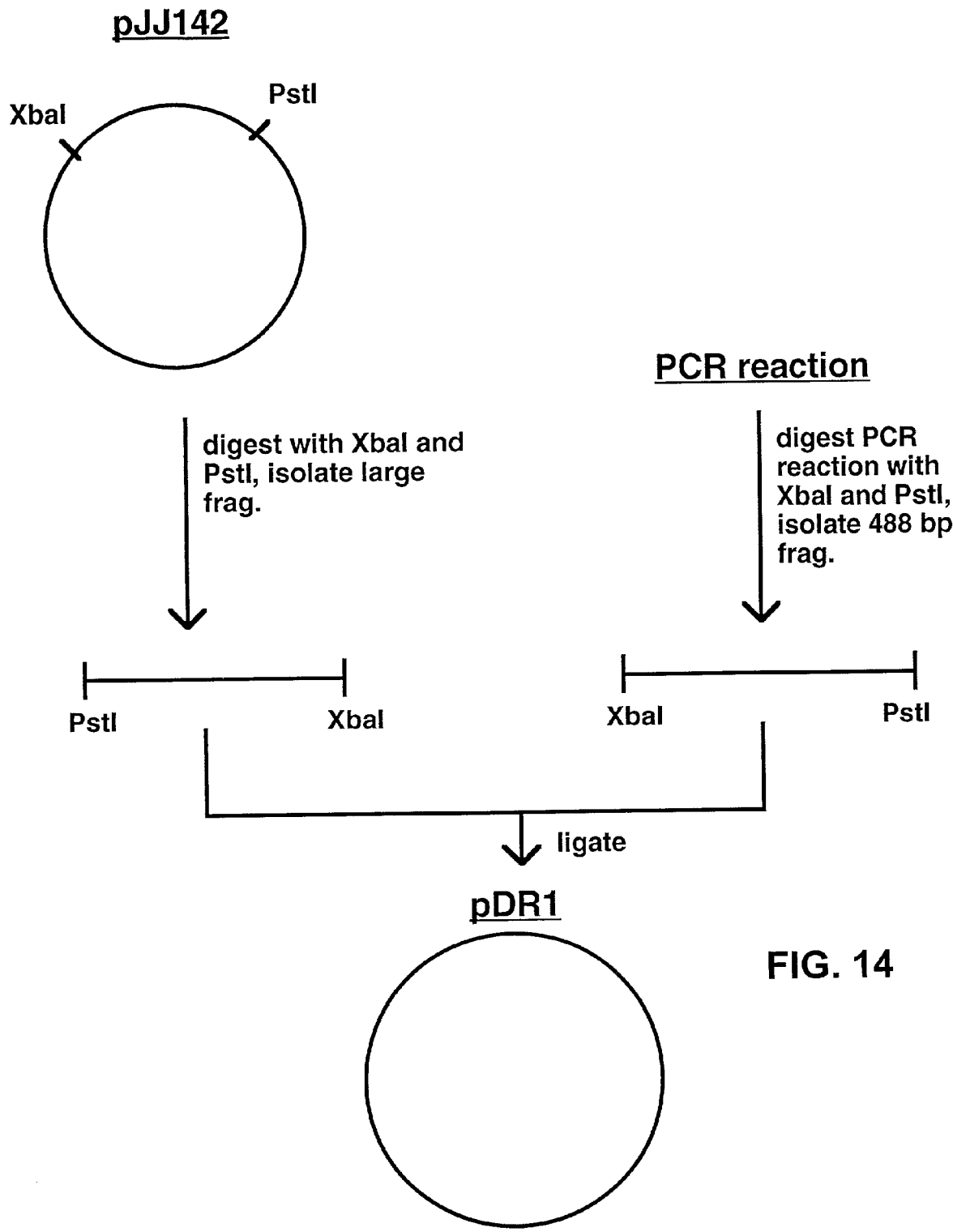
FIG. 14 shows the construction of plasmid pDR1.

The plasmid pDR1 is designed to express GreB under the control of the tacII promoter. pDR1 was constructed as shown in FIG. 14 by the ligation of two DNA fragments. The first of these was the vector pJJ142 in which the small XbaI-PstI fragment had been removed. The second part was a 488-base-pair XbaI-PstI fragment containing the greB gene. This fragment was prepared by first amplifying the greB coding sequence by PCR using *E coli* chromosomal DNA and then digesting this mixture with XbaI and PstI. The following primers were used for this step:

5'-CCCCCCCCCTCTAGAAAAATGAAAACTCCTCTG (SEQ ID NO:15)
GTAACGCGGGAAGGG

5'-CCCCCCCCCCTGCAGTTACGGTTTCACGTACTC (SEQ ID NO:16)
GATAGC

Plasmid pDR3

Figure 15:
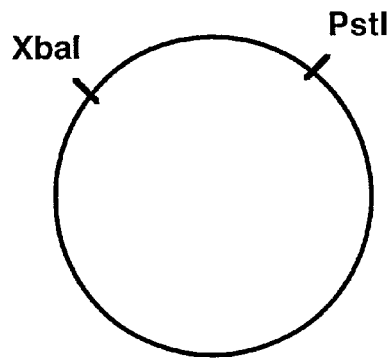
FIG. 15 shows the construction of plasmid pDR3.
Figure 15:
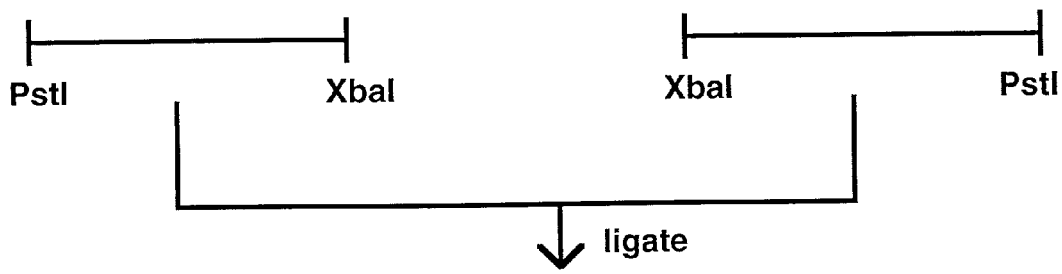
Figure 15:
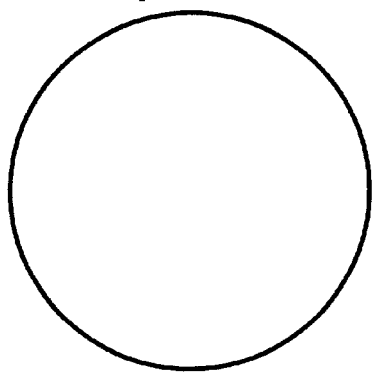

The plasmid pDR3 is designed to express GreA under the control of the tacII promoter. pDR3 was constructed as shown in FIG. 15 by the ligation of two DNA fragments. The first of these was the vector pJJ142 in which the small XbaI-PstI fragment had been removed. The second part was a 491-base-pair XbaI-PstI fragment containing the greA gene. This fragment was prepared by first amplifying the greA coding sequence by PCR using *E coli* chromosomal DNA and then digesting this mixture with XbaI and PstI. The following primers were used for this step:

5'-CCCCCCCCCTCTAGAATTCTATGCAAGCTATTC (SEQ ID NO:17)
CGATGACCTTA

5'-CCCCCCCCCCTGCAGTTACAGGTATTCCACCTT (SEQ ID NO:18)
AAT

*E. coli* Host

The strain 52A7, which is a derivative of W3110 (ATCC 27,325) having the genotype tonAΔ (fhuAΔ) lonΔ galE rpohts (htpRts) ΔclpP lacIq, was used for the transformation experiments.

Transformation and Culturing

For determining if λN anti-termination had any effects on the truncation and 10Sa tagging of TPO, the trp expression vector pMP331 and the anti-termination plasmids with low (pMP951) and high levels (pMP1217) of N expression were transformed into strain 52A7 using standard procedures. All these transformants were grown in Luria Broth (LB) media with ampicillin overnight at 30° C., and then diluted 20 fold into M9 with casamino acids media also containing ampicillin. After approximately 6 hours at 30° C. with shaking, the optical density of the cultures (600 nm) was between 2 and 2.5, and isopropyl β-D-thiogalactopyranoside (IPTG) (1 mM) was added to the two anti-termination cultures pMP951 and pMP1217. All cultures were then grown an additional 15 hours with shaking at 30° C. Samples were then removed, prepared as described in Yansura et al., *Methods in Mol. Biol.*, 62: 44–62 (1997), and analyzed by SDS-PAGE.

TPO expression with the AP promoter was then tested to see if similar results would be obtained with λN antitermination. The AP expression plasmid pMP1099 as well as the anti-termination plasmids with low-(pMP1086) and high-level (pMP1201) N expression were first transformed into the *E. coli* strain 52A7. Transformants were first grown in LB media containing ampicillin overnight at 30° C., and then diluted 100 fold into a phosphate-limiting media called C.R.A.P., which also contains ampicillin. (C.R.A.P. medium contains 3.57 g $(NH_4)_2SO_4$, 0.71 g NaCitrate-$2H_2O$, 1.07 g KCl, 5.36 g yeast extract (Certified), 5.36 g HY-CASE® SF refined acid-hydrolyzed casein (Quest International), 110 mL 1M morpholino propane sulfonic acid (MOPS) pH 7.3, 11 mL of a 50% glucose solution, and 7 mL 1M $MgSO_4$ in a final volume of 1 liter). After growth at 30° C. for approximately 6 hours, the cultures reached an optical density (600 nm) of between 1.5 and 2.0, and IPTG (1 mM) was added to the two anti-termination plasmids. Growth at 30° C. was continued for another 15 hours, at which time samples were removed, prepared as described for the trp vectors, and analyzed by SDS-PAGE.

Results:

Production of TPO Using Control Plasmids pMP331 and pMP1099

Figure 16:
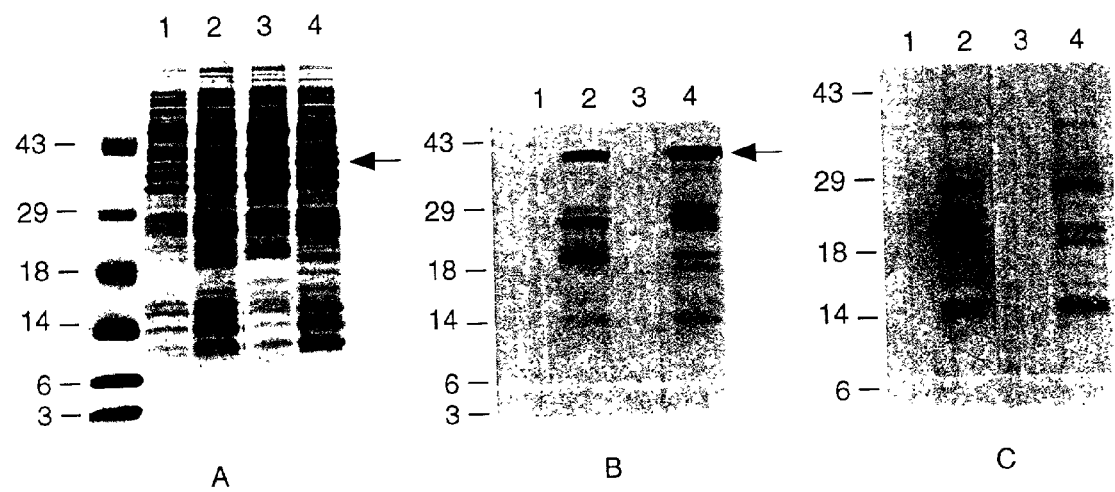
FIGS. 16A–16C show an analysis of thrombopoietin (TPO) expression under the transcriptional control of the tryptophan (trp) and alkaline phosphatase (AP or phoA) promoters. On the left are molecular weight markers in kDs. Lanes 1 are the negative control plasmid pBR322 after induction of the trp promoter in M9 media, lanes 2 are the trp TPO expression plasmid pMP331 after induction of the trp promoter, lanes 3 are the negative control plasmid pBR322 after induction of the AP promoter in C.R.A.P. media, and lanes 4 are the AP TPO expression plasmid pMP1099 after induction of the AP promoter.

TPO (de Sauvage et al., *Nature*, 369: 533–538 (1994)) was expressed in the cytoplasm of *E. coli* strain 52A7 under the control of both the trp (pMP331) and the AP (pMP1099) promoters with a small amino-terminal polyhis leader to provide for easy purification. Induction of either promoter trp or AP led to the production of TPO-related protein that could be detected by Coomassie-stained whole-cell extracts separated on an SDS polyacrylamide gel (SDS-PAGE), as shown in FIG. 16A.

Besides the expected protein band for the full-length polyhis leader-TPO at 37 kD, several other induced protein bands of lower molecular mass were noted. The most noticeable of these had masses of approximately 25, 18, and 14 kD. To determine if these lower-molecular-weight bands were TPO-related, the whole cell lysate was again separated by SDS-PAGE, transferred to nitrocellulose, and probed with an agent that binds to the polyhis motif on the leader (INDIA™ metal-chelated histidine probe bound to HRP (HisProbe-HRP) offered by Pierce Chemical Company) as shown in FIG. 16B. The results verified that the previously noted lower-molecular-weight bands were indeed TPO-related, and also revealed a much more severe truncation problem occurring on the C-terminal end of the protein.

To ascertain if these multiple truncated forms of TPO resulted from degradation of the polyhis leader containing full-length protein or were initially synthesized in this way, a pulse-chase analysis was performed using the same plasmid construct. Without limitation to any one theory, the results suggest that the latter case was the more likely explanation. The formation of truncated forms of TPO can clearly be seen showing up in the very early chase times of 0.5 and 1 minutes and remaining throughout the experiment up to 6 minutes. There was no obvious movement of TPO-related protein from full-length to truncated forms or vice-versa, suggesting that the lower-molecular-weight forms were produced directly during protein synthesis.

One possible explanation that needed to be ruled out was plasmid instability, particularly deletions in the TPO-coding sequence. Therefore, the plasmid DNA was isolated by induction culturing, with the resulting DNA subjected to PAGE analysis after digestion with several restriction endonucleases. In addition, individual colonies from the induction culture were analyzed in a similar fashion. In all cases there was no evidence of any plasmid alterations, particularly in the TPO-coding sequence.

Finally, the possibility of producing truncated TPO fragments by the translation of truncated mRNA was investigated. Such protein fragments had previously been shown to contain a C-terminal, 11-amino-acid tag encoded by a small open reading frame in the 10Sa RNA (Tu et al., supra; Keiler et al., supra). A polyclonal antibody directed against the chemically-synthesized tag was used to probe whole cell extracts from TPO induction cultures. The results in FIG. 16C clearly show that the majority of the truncated TPO fragments contained the 10Sa 11-amino-acid tag, and suggest, without limitation to any one theory, that the TPO mRNA is truncated or damaged.

Production of TPO Using Anti-Termination System and Effect on 10Sa Tagging

Although the expression of full-length TPO with the N-terminal polyhis leader was relatively high with both the trp and the AP promoters, the accumulation of truncated forms of TPO greatly interfered with protein purification. Since all of the truncated forms have the N-terminal polyhis leader, they co-purify with the full-length protein on a metal chelation column. Elimination of these truncated forms therefore becomes an important factor in the purification and production of a protein such as TPO.

Despite the failure of rrnB anti-termination to work for this purpose (Makrides, supra), a different transcription anti-termination agent, λN, was used in this Example to minimize or eliminate the truncation and 10Sa tagging of TPO by promoting transcriptional readthrough of intragenic termination signals within the TPO coding sequence.

Incorporating λN Anti-Termination

Figure 17:
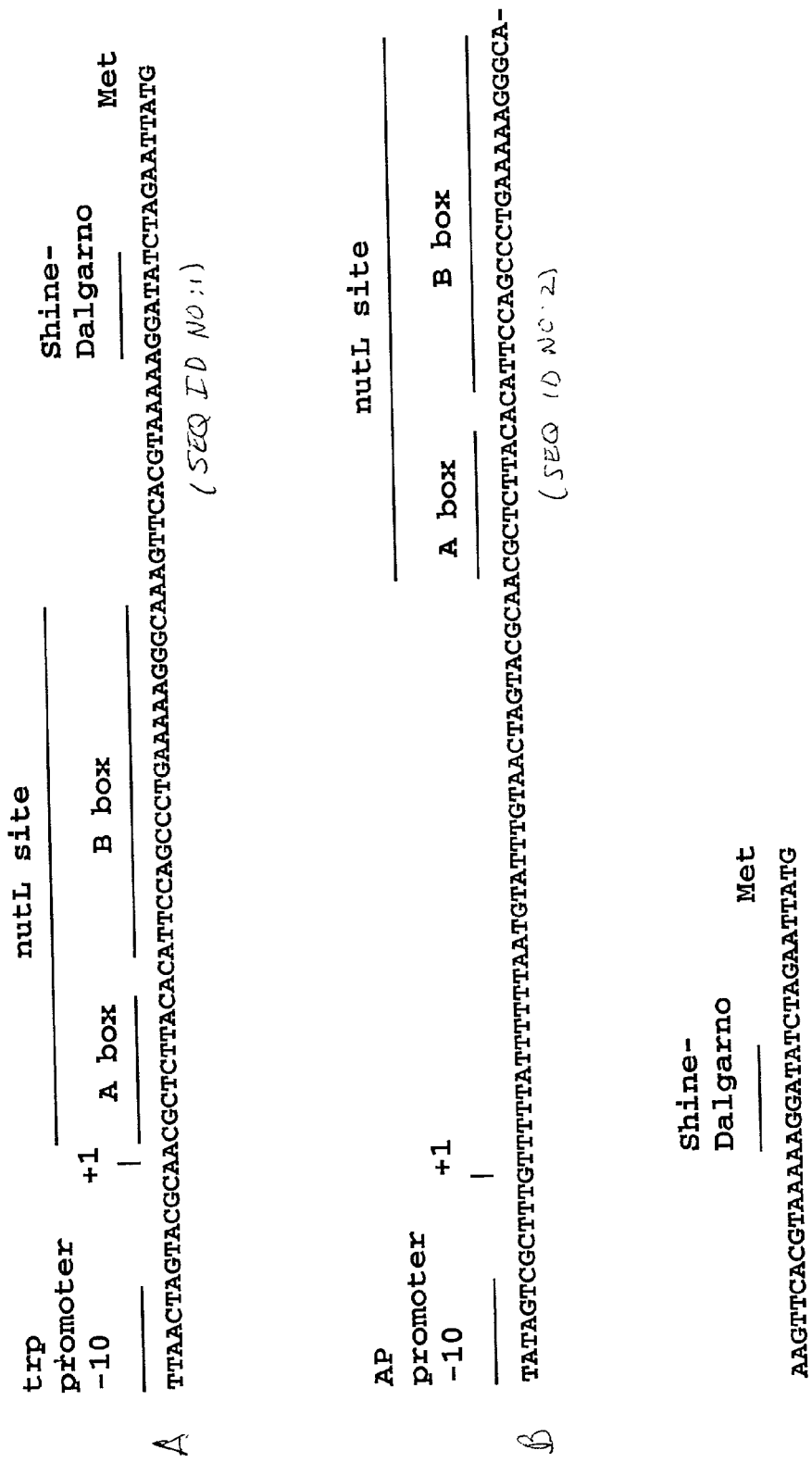
FIGS. 17A and 17B respectively show the insertion of a nutL site into the trp (SEQ ID NO:1) and AP (SEQ ID NO:2) TPO expression constructs. In the FIG. 17A sequence, the nutL sequence was inserted at the beginning of the mRNA sequence based on the promoter –10 box. The FIG. 17B sequence shows the insertion of the nutL site into the AP promoter construct. Here, the nut site is situated further downstream from the mRNA start site.
Figure 18:
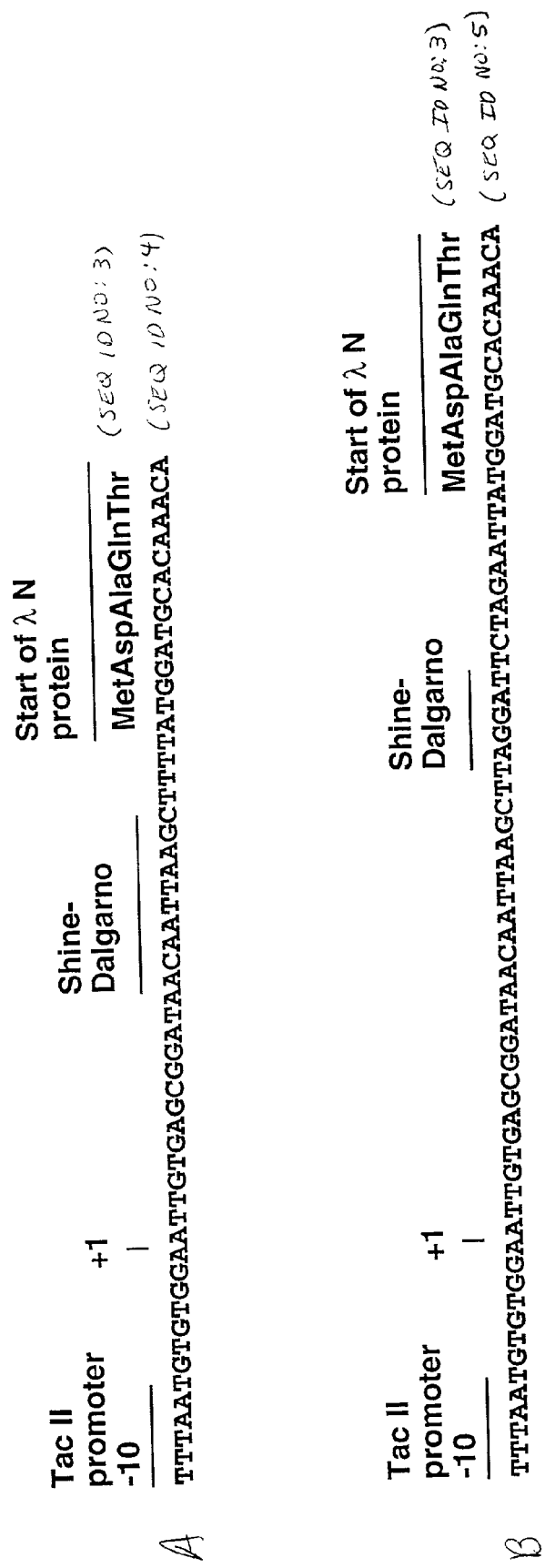
FIGS. 18A and 18B show the expression of λN protein under the transcriptional control of the tacII promoter. The start sequence of the λN protein is shown in each of FIGS. 18A and 18B (SEQ ID NO:3). The FIG. 18A nucleotide sequence (SEQ ID NO:4) shows the fusion of the tacII promoter to the λN coding sequence. In this case the tacII Shine-Dalgarno sequence has been deleted to provide for reduced λN translation, and an alternative sequence with lower 16S ribosomal RNA binding is used. The FIG. 18B nucleotide sequence (SEQ ID NO:5) shows the fusion of the tacII promoter to the λN gene using the complete Shine-Dalgarno sequence for high-level N expression.

To incorporate λN anti-termination into the trp and AP expression systems for TPO, the N utilization sequence (nutL) was first inserted into the plasmids at locations corresponding to the beginning of the TPO mRNA. The actual design of these sequences, including the upstream promoters and the downstream polyhis leader, is shown in FIG. 17. The λN gene was then inserted into these plasmids downstream of the TPO coding sequence and the $λt_o$ transcriptional terminator. N expression was placed under the control of the tacII promoter (DeBoer et al., (1983), supra), and plasmids with and without the tacII Shine-Dalgarno sequences were constructed. This variation in the translation of N provided an easy way to look at two different expression levels of N, and their subsequent effects on TPO expression. Partial sequences showing the tacII promoter with and without the Shine-Dalgarno sequence are shown in FIG. 18.

Effects of λN Anti-Termination on TPO Expression

Figure 19:
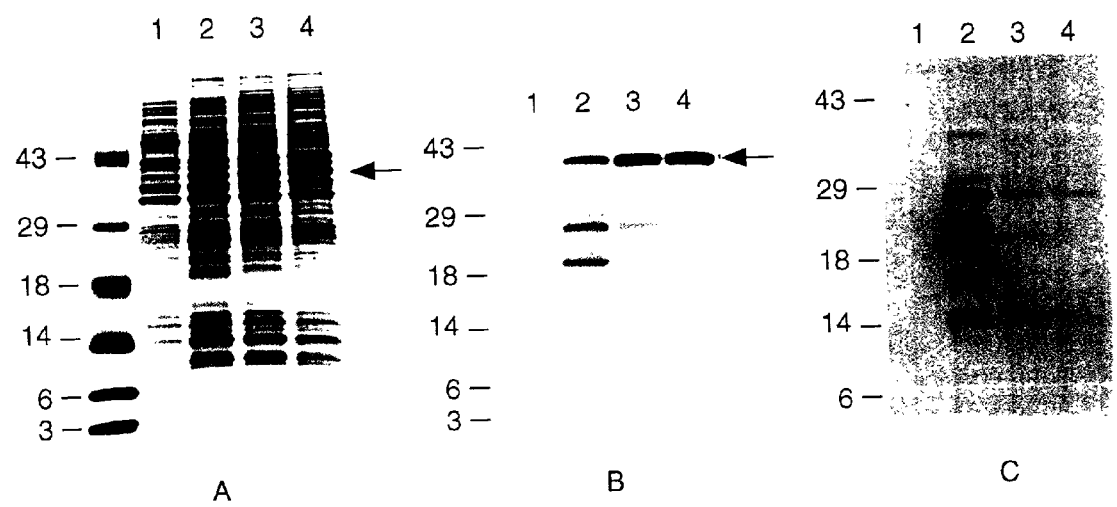
FIGS. 19A–19C show an analysis of TPO expression with the trp promoter+/–λN anti-termination. On the left are molecular weight markers in kDs. Lanes 1 are the negative control plasmid pBR322, lanes 2 are the trp TPO expression plasmid pMP331, lanes 3 are the trp TPO expression plasmid pMP951 with λN anti-termination and low-level N expression, and lanes 4 are the trp TPO expression plasmid pMP1217 with λN anti-termination and the high-level expression of N.

Coomassie staining of the SDS gels for the trp expression plasmids pMP331, pMP951, and pMP1217 revealed primarily an increase in the expression of full-length TPO with both low-level (pMP951) and high-level (pMP1217) N expression as compared with the control (pMP331) as shown in FIG. 19A. Analysis of the SDS gel, after transferring to nitrocellulose and probing with HisProbe-HRP, showed not only an increase in the expression of full-length TPO, but also a significant decrease in the formation of truncated forms of TPO for both anti-termination plasmids (FIG. 19B). Finally, an analysis of the gel after transferring to nitrocellulose and probing with antibody to the 10Sa tag also showed a significant decrease in the accumulation of truncated and 10Sa-tagged forms of TPO with both anti-termination plasmids (FIG. 19C).

Figure 20:
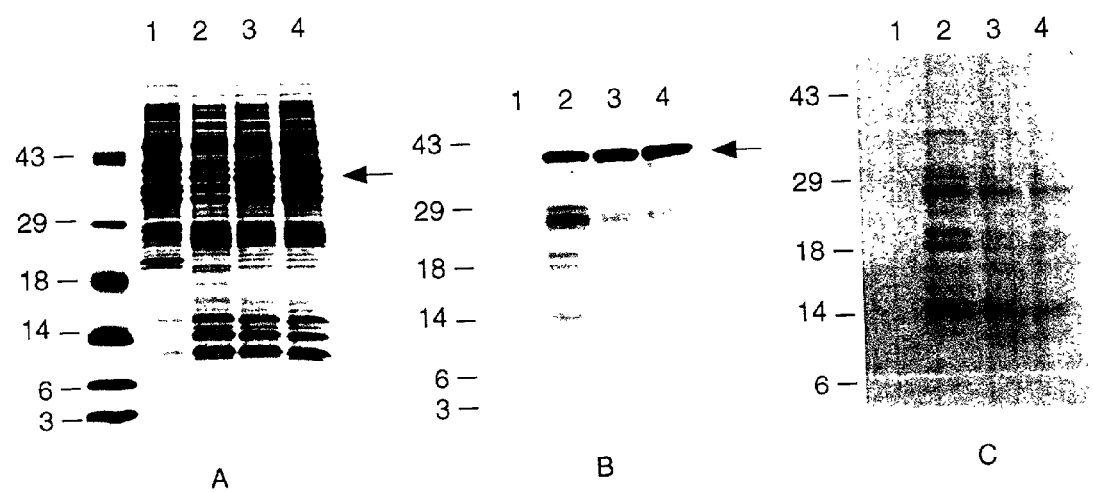
FIGS. 20A–20C show an analysis of TPO expression with the AP promoter+/–λN anti-termination. On the left are molecular weight markers in kDs. Lanes 1 are the negative control plasmid pBR322, lanes 2 are the AP TPO expression plasmid pMP1099, lanes 3 are the AP TPO expression plasmid pMP1086 with λN anti-termination and the low-level N expression, and lanes 4 are the AP TPO expression plasmid pMP1201 with λN anti-termination and the high-level expression of N.

Coomassie staining of the SDS gels for the AP expression plasmids pMP1099, pMP1086, and pMP1201 showed an increase in the level of full-length TPO with both anti-termination plasmids as compared to the control plasmid pMP1099, as was seen with the trp plasmids (FIG. 20A). After transferring to nitrocellulose and probing with His-Probe-HRP, one can also see an increase in the level of full-length TPO as well as a significant decrease in the expression of truncated forms of TPO (FIG. 20B). In a similar analysis, probing with the anti-10Sa antibody showed a decrease in the accumulation of truncated and 10Sa-tagged forms of TPO with both anti-termination plasmids (FIG. 20C).

Conclusion

It is clear from the above shake-flask results that the presence of λN anti-termination with low or high amounts of N proteins using either promoter increased the titer of the polypeptide. Further, the presence of the λN protein anti-termination system in low or high amounts with either promoter reduced the amount of 10Sa-tagged protein made by the cells.

EXAMPLE 2

Effect of N Anti-Termination System on TPO Production (Fermentor)

Materials and Methods:

Transformation

The strain 52A7 was transformed with each of pMP331, pMP951, pMP1099, or pMP1086, each of which is described above in Example 1, using standard procedures involving ampicillin or tetracycline as appropriate.

Culture of Transformed Cells

Example for pMP331 and pMP951:

A 10-liter fermentation was carried out in the following medium, with modifications as noted. A bag of salts suitable for a 10-liter fermentation contained the following salts:

| Salt | Grams |
| --- | --- |
| Ammonium Sulfate | 50.0 |
| Potassium Phosphate, dibasic | 60.0 |
| Sodium Phosphate, monobasic dihydrate | 30.0 |
| Sodium Citrate, dihydrate | 10.0 |

In addition to the salts, 5 g L-isoleucine and 3 mL of a 25% solution of PLURONIC® L-61 antifoam polyol (BASF Corporation) were added to the fermentor. The fermentor was sterilized with these components and 5–6.5 liters of deionized water. After the fermentor and contents cooled down, the post-sterile ingredients were added. The post-sterile ingredients consisted of 15 mL of a 50% glucose solution, 70 mL of 1 M magnesium sulfate, 5 mL of trace metals (recipe below), 250 mL of 20% HY-CASE® acid-hydrolyzed casein solution, 250 mL of 20% yeast extract solution, and 250 mL of a 2 mg/mL ampicillin solution. The starting volume in the fermentor, after inoculation, was usually 8.5 liters.

The fermentor was inoculated with 500 mL of a 16–20-hour LB culture that had been grown with agitation at 30° C. The LB culture was grown in the presence of ampicillin. The 10-liter culture was agitated at 750 rpm and aerated at 10 slpm. The culture pH was maintained at 7.0–7.3 by the automatic addition of ammonium hydroxide, and the temperature was maintained at 30° C. When the initial glucose in the culture was exhausted, a glucose feed was started and maintained at such a rate as to prevent starvation and also to avoid accumulation of glucose in the medium.

Culture growth was monitored by measuring the optical density (O.D.) at a wavelength of 550 nm. When the culture O.D. reached 25–35, 25 mL of a 25 mg/mL solution of 3-β-indole acrylic acid (IAA) and 2–50 mL of a 200 mM IPTG solution (for pMP951 only) were added. The cell paste was harvested via centrifugation 14–18 hours after IAA addition.

| Trace Element | Amounts |
| --- | --- |
| Hydrochloric Acid | 100 mL |
| Ferric Chloride hexahydrate | 27 g/L |
| Zinc Sulphate heptahydrate | 8 g/L |
| Cobalt Chloride hexahydrate | 7 g/L |
| Sodium Molybdate | 7 g/L |
| Cupric Sulphate pentahydrate | 8 g/L |
| Boric Acid | 2 g/L |
| Manganese Sulphate monohydrate | 5 g/L |
| Deionized Water | to 1 liter |

Example for pMP1099 and pMP1086:

A 10-liter fermentation was carried out in the following medium, with modifications as noted. A bag of salts suitable for a 10-liter fermentation contained the following salts:

| Salt | Grams |
| --- | --- |
| Ammonium Sulfate | 50.0 |
| Potassium Phosphate, dibasic | 26.0 |
| Sodium Phosphate, monobasic, dihydrate | 13.0 |
| Sodium Citrate, dihydrate | 10.0 |
| Potassium Chloride | 15.0 |

In addition to the salts, 5 g L-isoleucine and 3 mL of a 25% solution of PLURONIC® L-61 antifoam polyol (BASF Corporation) were added to the fermentor. The fermentor was sterilized with these components and 5–6.5 liters of deionized water. After the fermentor and contents cooled down, the post-sterile ingredients were added. The post-sterile ingredients consisted of 15 mL of a 50% glucose solution, 70 mL of 1 M magnesium sulfate, 5 mL of trace metals (recipe below), 250 mL of 20% HY-CASE® acid-hydrolyzed casein solution, 250 mL of 20% yeast extract solution, and 250 mL of a 2 mg/mL-ampicillin solution. The starting volume in the fermentor, after inoculation, was usually 8.5 liters.

The fermentor was inoculated with 500 mL of a 16–20-hour LB culture that had been grown with agitation at 30° C. The LB culture was grown in the presence of ampicillin. The 10-liter culture was agitated at 750 rpm and aerated at 10 slpm. The culture pH was maintained at 7.0–7.3 by the automatic addition of ammonium hydroxide, and the temperature was maintained at 30° C. When the initial glucose in the culture was exhausted, a glucose feed was started and maintained at such a rate as to prevent starvation and also to avoid accumulation of glucose in the medium.

Culture growth was monitored by measuring the O.D. at a wavelength of 550 nm. When the culture O.D. reached 25–35, 2–50 mL of a 200 mM IPTG solution (for pMP1086 only) was added. The cell paste was harvested via centrifugation 20–30 hours after inoculation.

| Trace Element | Amounts |
|---|---|
| Hydrochloric Acid | 100 mL |
| Ferric Chloride hexahydrate | 27 g/L |
| Zinc Sulphate heptahydrate | 8 g/L |
| Cobalt Chloride hexahydrate | 7 g/L |
| Sodium Molybdate | 7 g/L |
| Cupric Sulphate pentahydrate | 8 g/L |
| Boric Acid | 2 g/L |
| Manganese Sulphate monohydrate | 5 g/L |
| Deionized Water | to 1 liter |

Generation of Polyclonal and Monoclonal Antibodies to the 10Sa Peptide:

The following peptide was synthesized for generating antibodies: CAANDENYALAA (SEQ ID NO:19). The N-terminal cysteine is present to allow conjugation of the peptide to either KLH or soybean trypsin inhibitor, or another suitable conjugation partner. The remaining residues are encoded by the ssrA gene from *E. coli* and translate to give the 10Sa peptide. The above peptide was synthesized and conjugated to KLH by Zymed Corporation and used as the antigen to raise antibodies in both rabbits and mice.

Specific antibodies to the 10Sa peptide were obtained by taking either serum from rabbits injected with the antigen or ascites fluid from mice. The serum or ascites fluid was passed over an affinity column that had the synthetic 10Sa peptide bound to it. The specific antibodies were eluted from the 10Sa affinity column using low pH.

Quantitation of 10Sa-Tagged and Full-Length TPO:

TPO fusion proteins made from the plasmids pMP331, pMP951, pMP1099, and pMP1086 were extracted from whole cell pellets using a buffer containing 7.5 M guanidine HCl, 0.1 M sodium sulfite, 0.02 M sodium tetrathionate, and 50 mM Tris buffer, pH 8.0. Extractions were allowed to continue 1–16 hours with stirring at room temperature. The extracted solution was then clarified with centrifugation and the supernatant dialyzed 1–16 hours at 4° C. against a buffer containing 6 M GuHCl and 20 mM Tris buffer, pH 7.5. The polyhis-containing proteins from the dialysate were purified via a chelating column (Talon Metal Affinity Resins, Clontech). The protein eluted from the column was run on SDS-PAGE, transferred to nitrocellulose, and probed with a polyclonal antibody raised against either $TPO_{153}$ (WO 95/18858 published Jul. 13, 1995) or the 10Sa peptide. The blots were then scanned using an optically enhanced laser densitometer (PDI Inc., model 325oe). The peak areas for the full-length TPO, as well as the other TPO species that cross-react with the $TPO_{153}$ polyclonal antibody, were determined.

Results:

The results from these analyses are shown in Table 1. The ratio of full-length TPO to all of the TPO species was calculated and is reported as % TPO. In addition, the total peak area detected on the blot probed with the polyclonal antibody raised to the 10Sa peptide was also calculated and is reported as 10Sa tag.

TABLE 1

Effect of Plasmid Construct on TPO332 Accumulation and 10Sa Tagging

| Plasmid | Nut Site | N Protein | % TPO | 10Sa Tag |
|---|---|---|---|---|
| pMP331 | − | − | 4.5 | 11.5 |
| pMP951 | + | + | 49.0 | 2.6 |
| pMP1099 | − | − | 50.0 | 4.6 |
| pMP1086 | + | + | 73.0 | 1.6 |

The data in Table 1 show that expressing TPO from a plasmid with the λN anti-termination system resulted in an increased percentage of TPO that is full-length TPO and a decrease in accumulated 10Sa tagged TPO. This is seen whether the AP or the trp promoter is used to control TPO expression.

EXAMPLE 3

Effect of GreA or GreB on TPO Production (Shake-Flask)

Materials and Methods:

Transformations

The strain 59B9 (W3110 fhuAΔ (tonAΔ) lonΔ galE rpohts (htpRts) ΔclpP lacIq ΔompT Δ(nmpc-fepE) ΔlacY) was transformed with each of pMP331, pMP951, pMP1217, pMP1099, pMP1086, or pMP1201 either alone or in combination with pDR1 or pDR3, each of which is described above in Example 1, using standard procedures.

Culture of Transformed Cells

The transformed cells were grown in LB media with ampicillin and kanamycin (when co-transformed with pDR1 or pDR3 only) at 30° C. with shaking overnight and then diluted 50-fold into shake-flask culture medium containing ampicillin and grown at 30° C. with shaking. Transformants containing the plasmids pMP331, pMP951, or pMP1217 were grown in THCD medium with the appropriate antibiotic until they reached an O.D.550 of 1–2, at which time IAA (50 μg/ml final concentration) and IPTG (1 mM, final concentration) (for pMP951 and pMP1217 only) were added to the culture. All cultures were grown for a total of 24 hours. Samples were then removed and prepared for SDS-PAGE.

THCD medium contains 1.86 g $Na_2HPO_4$, 0.93 g $NaH_2PO_4$—$H_2O$, 3.57 g $(NH_4)_2SO_4$, 0.71 g NaCitrate-$2H_2O$, 1.07 g KCl, 5.36 g yeast extract (Difco® Bacto® brand, #0127-01-7), 5.36 g casamino acids (Difco® Bacto® brand, #0230-17-3), 7 mL of 1M $MgSO_4$, 11 mL of a 50% glucose solution, and 110 mL 1 M MOPS, pH 7.3, in a final volume of 1 liter.

Transformants containing the plasmids pMP1099, pMP1086, or pMP1201 with or without either pDR1 or pDR3 were grown in C.R.A.P. medium with the appropriate antibiotics until they reached an O.D.550 of 1–2, at which time IPTG (1 mM final concentration) was added to all of the cultures except for the one containing pMP1099 alone. All cultures were grown for a total of 24 hours. Samples were then removed and prepared for SDS-PAGE.

Quantitation of 10Sa-Tagged and Full-Length TPO

Samples from the shake-flask cultures described above were prepared and run on SDS-PAGE, transferred to nitrocellulose, and probed with a polyclonal antibody raised against either $TPO_{153}$ or the 10Sa peptide. The blots were then scanned using an optically enhanced laser densitometer (PDI, Inc., model 325oe). The peak areas for the full-length TPO, as well as the other TPO species that cross-react with the $TPO_{53}$ polyclonal antibody, were determined.

The same set of shake-flask samples was also run on SDS-PAGE and stained with Coomassie Blue. The gels were scanned using an optically enhanced laser densitometer (PDI, Inc., model 325oe) and the percentage of total cell protein represented as full-length TPO was calculated.

Results:

The results from these analyses are shown in Table 2, where SD signifies the Shine-Dalgarno sequence. The ratio of full-length TPO to all of the TPO species was calculated and is reported as % TPO. In addition, the total peak area detected on the blot probed with the polyclonal antibody raised to the 10Sa peptide was also calculated and is reported as 10Sa tag. The percentage of total cell protein represented as full-length TPO is shown as % of total protein.

TABLE 2

Effect of Plasmid Construct on TPO332 Accumulation and 10Sa Tagging

| Plasmid(s) | Nut Site | N Protein | % of total protein | % TPO | 10Sa Tag |
|---|---|---|---|---|---|
| pMP331 | − | − | 5.8 | 11.3 | 7.6 |
| pMP951 | + | +, no SD | 5.8 | 30.9 | 2.5 |
| pMP1217 | + | +, full SD | 5.0 | 33.0 | 1.7 |
| pMP1099 | − | − | 6.1 | 17.8 | 3.3 |
| pMP1099/pDR1 | − | − | 8.2 | 21.2 | 4.2 |
| pMP1099/pDR3 | − | − | 8.2 | 21.2 | 4.8 |
| pMP1086 | + | +, no SD | 7.3 | 27.6 | 2.3 |
| pMP1086/pDR1 | + | +, no SD | 7.7 | 37.5 | 2.0 |
| pMP1086/pDR3 | + | +, no SD | 8.5 | 32.0 | 2.9 |
| pMP1201 | + | +, full SD | 6.8 | 43.7 | 1.6 |

The data in Table 2 show that expressing TPO from a plasmid with the λN anti-termination system results in a dramatic decrease in 10Sa-tagged TPO, as reflected in the column labeled 10Sa Tag. The percentage of TPO present as full-length TPO also increases with the λN anti-termination system (% TPO column of Table 2).

It is noted that the control plasmid with the AP promoter (pMP1099), but not with the trp promoter (pMP331), produced more % TPO in the fermentor than in the shake flask (compare Table 1 to Table 2). The fermentor conditions provide a more constant glucose feed and controlled pH with a longer induction period than the shake-flask conditions, so that more protein is produced in the former, using the AP promoter. However, with the anti-termination system, the results show a consistent improved trend in % TPO whether the TPO is produced in the shake flasks or in the fermenter and whether the promoter is trp or AP. Moreover, the 10Sa tag is lower for the anti-termination system in all cases.

Further, it is clear from the data that co-expressing TPO and either GreA or GreB with or without the λN anti-termination system results in an increase in TPO production (% of total protein column in Table 2). There is also an increase in the percentage of TPO present as full-length TPO when either GreA or GreB is co-expressed with TPO.

EXAMPLE 4

Effect of N Anti-Termination System on FGF-5 Production (Fermentor)

Materials and Methods:

Description and Construction of the FGF-5 Expression Plasmids

Plasmid pFGF5IT

The hFGF-5 *E. coli* expression plasmid, pFGF5IT, was constructed from a basic backbone of pBR322 (Sutcliffe, *Cold Spring Harb Symp Quant Biol.*, 43: 77–90 (1978)). The trp promoter provides the transcriptional sequence required for efficient expression of the FGF-5 gene in *E. coli* (Yanofsky et al., *Nucleic Acids Res.*, 9: 6647–6668 (1981)). Two Shine-Dalgarno sequences, the trp Shine-Dalgarno and a second Shine-Dalgarno, facilitated the translation of FGF-5 mRNA (Yanofsky et al., *Nucleic Acids Res.*, 9: 6647–6668 (1981); Ringquist et al., *Molecular Microbiol.*, 6: 1219–1229 (1992)). The coding sequence for mature FGF-5 (lacking the wild-type signal sequence) is located downstream of the promoter and Shine-Dalgarno sequences and is preceded by a methionine initiation codon.

Figure 21:
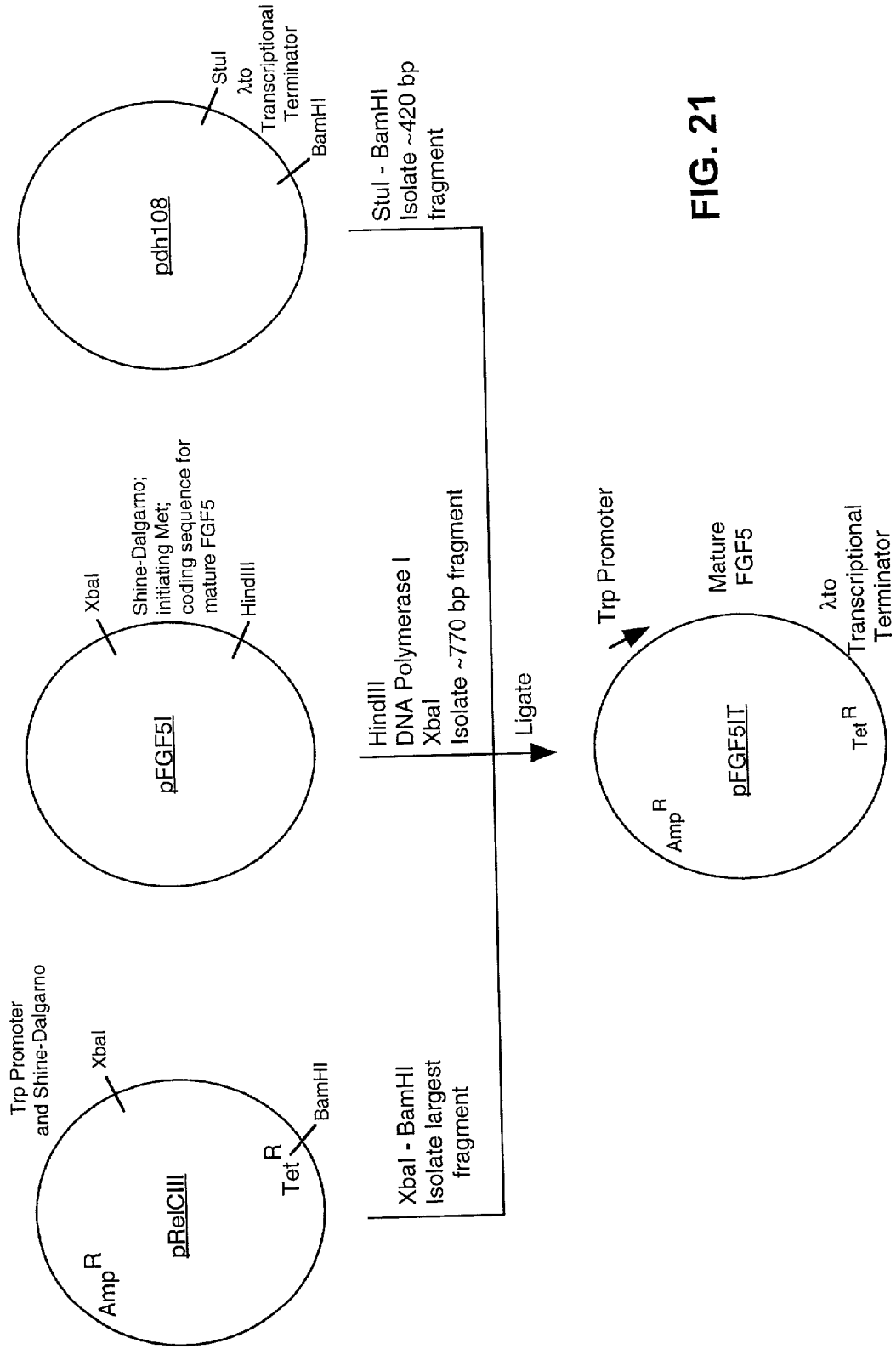
FIG. 21 shows the construction of plasmid pFGF5IT.

The vector used for the construction of pFGF5IT was generated by isolating the largest fragment when pRelCIII was digested with XbaI and BamHI. This vector contains the trp promoter and trp Shine-Dalgarno sequence. The second fragment required for this construction was isolated by first digesting pFGF5I with HindIII followed by treatment with DNA Polymerase I (Klenow fragment) to create a blunt end. This reaction was then digested with XbaI, resulting in a fragment of about 770 bp with one sticky end (XbaI) and one blunt end (HindIII Pol). This fragment contains a Shine-Dalgarno sequence, an initiation methionine codon, and the coding sequence for mature hFGF-5. The final fragment required for this construction was isolated from pdh108. This StuI-BamHI fragment of about 420 bp contains the sequence encoding the $\lambda t_o$ transcriptional terminator (Scholtissek et al., *Nucleic Acids Res.*, 15 (7): 3185 (1987)) and approximately the first 375 bp of pBR322 (Sutcliffe, supra). These three fragments were ligated together as depicted in FIG. 21 for the construction of pFGF5IT.

Plasmid pFGF5IT-AT

Figure 22:
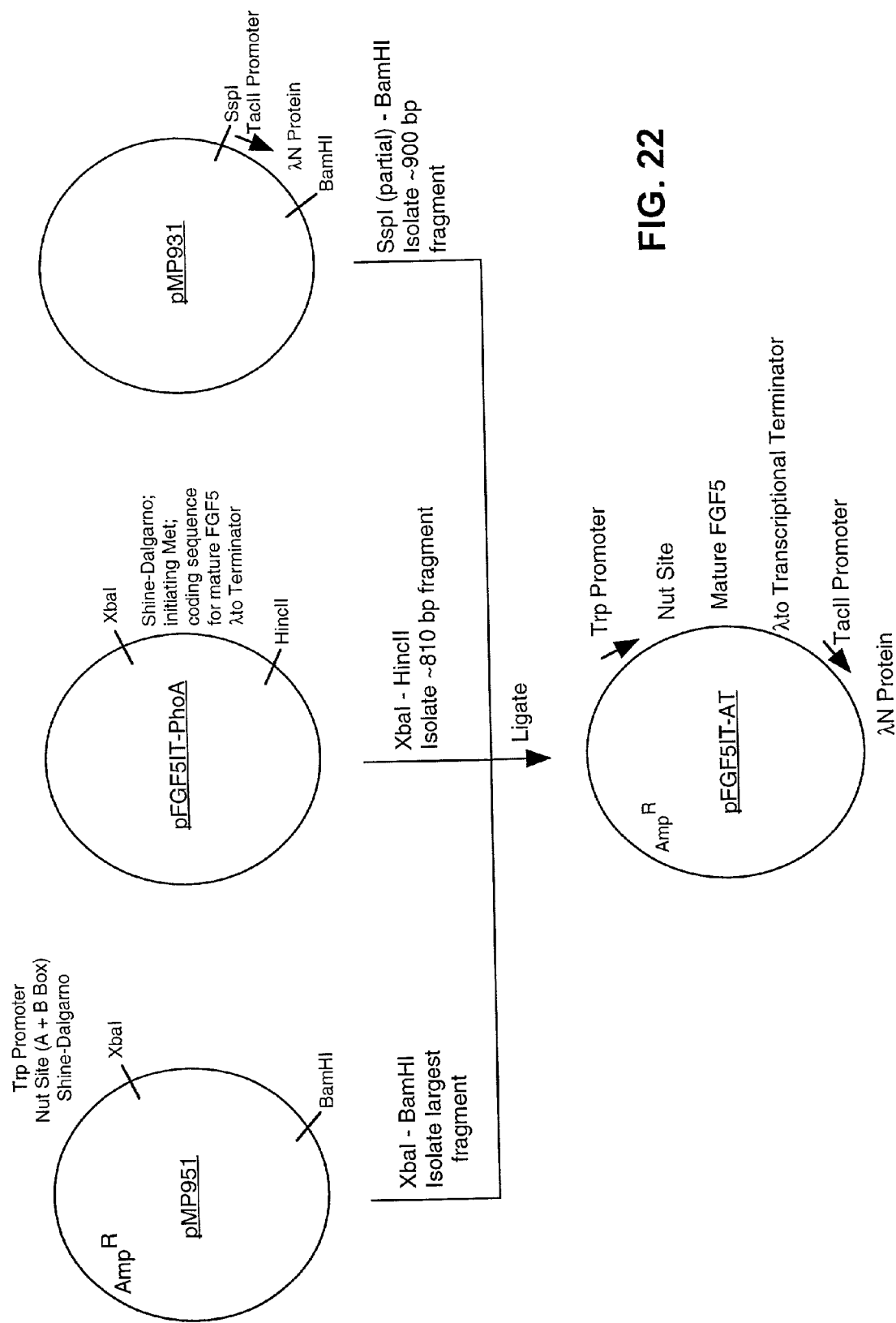

The plasmid pFGF5IT-AT simply places the coding sequence for FGF-5 into a λN anti-termination expression plasmid. The vector used for this construction was created by isolating the largest fragment when pMP951 was digested with XbaI and BamHI. This vector contains the trp promoter and the nut site (Boxes A+B). The second fragment required for this construction was isolated following digestion of pFGF5IT-PhoA with XbaI and HincII. The plasmid pFGF5IT-PhoA is a derivative of pFGF5IT in which the trp promoter is replaced by the AP promoter (Kikuchi et al., supra). This approximately 810-bp fragment contains a Shine-Dalgarno sequence, a methionine initiation codon, the coding sequence for mature hFGF5, and the sequence for the $\lambda t_o$ transcriptional terminator. The final fragment required for the ligation was isolated by digestion of pMP931 with SspI and BamHI. The SspI digestion was only a partial digestion, resulting in a fragment of approximately 900 bp. This last fragment contains the tacII promoter (without a Shine-Dalgarno) followed downstream by the coding sequence for λN protein. These three fragments were ligated together as illustrated in FIG. 22 to yield the plasmid pFGF5IT-AT.

Transformation

The strain 54C2 (*E. coli* W3110 fhuA(tonA)lon galE rpoHts(htpRts) clpP lacIq) was transformed with each of pFGF5IT or pFGF5IT-AT using standard procedures involving ampicillin.

Culture of Transformed Cells

The transformed cells were grown up in a fermenter under conditions described in Example 2 for the trp plasmids pMP331 and pMP951, except that the IPTG solution was used only for pFGF5IT-AT and not for pFGF5IT. Whole-cell lysates from the fermentation samples were prepared for SDS-PAGE.

Figure 23:
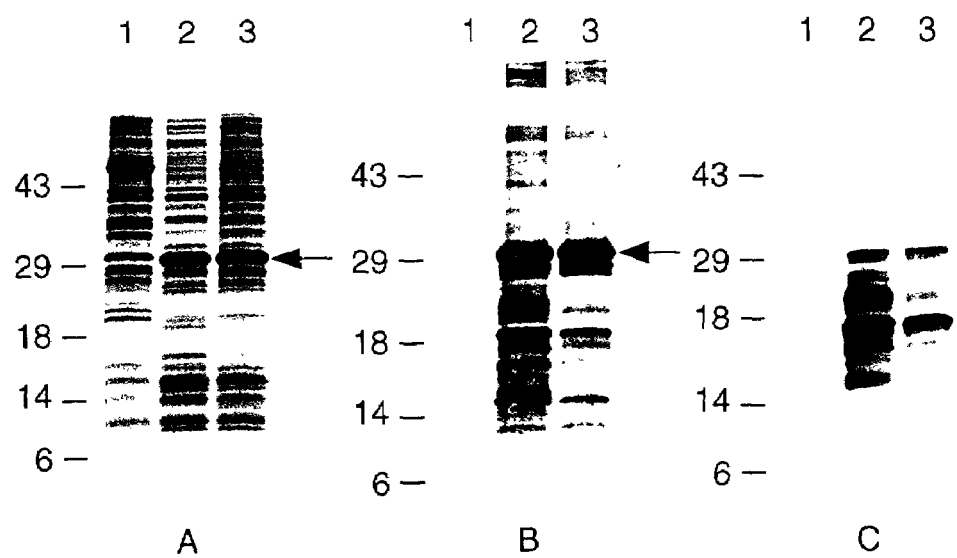
FIGS. 23A–23C show an analysis of FGF-5 expression+/–λN anti-termination. Lanes 1 are the negative control plasmid pBR322, lanes 2 are the expression of FGF-5 without λN anti-termination (pFGF5IT), and lanes 3 are the expression of FGF-5 with λN anti-termination (pFGF5IT-AT).

Results:

The FGF-5 intracellular expression plasmid pFGF5IT produced a significant amount of full-length protein (FIG. 23A, Lane 2). Despite this promising result, truncated FGF-5 species also accumulated in addition to the full-length protein (FIG. 23B, Lane 2), and the majority of these species were 10Sa-tagged (FIG. 23C, Lane 2). These results imply, without being limited to any one theory, that premature transcription termination is a likely source of the truncation problem.

To address this problem, the λN anti-termination system was co-expressed with the FGF-5 gene. The production of full-length FGF-5 was approximately equivalent for both plasmids, with or without λN anti-termination (FIG. 23A, lanes 2 and 3). However, the accumulation of truncated species was reduced by approximately 50% when the λN anti-termination system was co-expressed with the FGF-5-encoding gene (FIGS. 23B and 23C). The reduction of these truncated species not only allows for simplified purification of the FGF-5 full-length protein, but minimizing the production of these smaller FGF-5 fragments also leads to improved efficiency in refolding, since the smaller species may contribute to aggregation in the refolding reactions. In addition, any truncated species that do refold and remain in solution may complicate the assessment of bioactivity by interfering with the binding of full-length protein to the receptor. Thus, it is advantageous to reduce the level of premature transcription termination to prevent these potential problems from arising.

EXAMPLE 5

Effects of λN Anti-Termination and GreA/B on FGF-5 Production (Shake-Flask)

Materials and Methods:

Shake-Flask Experiments with FGF-5 and GreA or GreB Co-Expression:

The strain 59B9 {W3110 fhuAΔ(tonAΔ) lonΔ galE rpohts (htpRts) ΔclpP lacIq ΔompT Δ(nmpc-fepE) ΔlacY} was transformed with pFGF5IT-PhoA (described in Example 4) or pFGF5IT-PhoAAT, either alone or in combination with pDR1 or pDR3, each of which is described above. The plasmid pFGF5IT-PhoAAT is a derivative of pFGF5IT in which the same anti-termination element is present as in pEGE5IT-AT described in Example 4, and in which the trp promoter is replaced by the AP promoter (Kikuchi et al., supra).

Culture of the Transformed Cells

The transformed cells were grown in LB media with ampicillin and kanamycin (when co-transformed with pDR1 and pDR3 only) at 30° C. with shaking overnight and then diluted 50-fold into C.R.A.P. medium containing the appropriate antibiotics and grown at 30° C. with shaking. Transformants were grown in this medium until they reached an OD550 of 1–2, at which time IPTG was added (1 mM, final concentration) to all of the cultures except for the one containing pFGF5IT-PhoA alone. All cultures were grown for a total of 24 hours. Samples were then removed and prepared for SDS-PAGE.

Quantitation of 10Sa-Tagged and Full-Length FGF-5:

Samples from the shake-flask cultures described above were prepared and run on SDS-PAGE, transferred to nitrocellulose, and probed with a polyclonal antibody raised against either FGF-5 (R&D Systems) or the 10Sa peptide. The blots were then scanned using an optically enhanced laser densitometer (PDI, Inc., model 325oe). The peak areas for the full-length FGF-5, as well as the other FGF-5 species that cross-react with the FGF-5 polyclonal antibody, were determined.

Results:

The results from these analyses are shown in Table 3. The ratio of full-length FGF-5 to all of the FGF-5 species was calculated and is reported as % FGF-5. In addition, the total peak area detected on the blot probed with the polyclonal antibody raised to the 10Sa peptide was also calculated and is reported as 10Sa tag.

TABLE 3

Effect of Plasmid Construct on FGF-5 Accumulation and 10Sa Tagging

| Plasmid(s) | % FGF-5 | 10Sa Tag |
|---|---|---|
| pFGF5IT-PhoA | 15 | 10.6 |
| pFGP5IT-PhoA/ pDR1 | 16 | 11.3 |
| pFGF5IT-PhoA/ pDR3 | 21 | 7.6 |
| pFGF5IT-PhoAAT | 40 | 3.0 |
| pFGF5IT-PhoAAT/ pDR1 | 52 | 1.7 |
| pPGF5IT-PhoAAT/ pDR3 | 45 | 3.4 |

The data in Table 3 show that expressing FGF-5 from a plasmid with the λN anti-termination system results in a dramatic decrease in 10Sa-tagged FGF-5, as demonstrated by the scan data for 10Sa-tagged proteins in Table 3. The percentage of FGF-5 present as full-length FGF-5 also increases with the λN anti-termination system.

Further, it is clear from the data that co-expressing FGF-5 with either GreA or GreB with or without the λN anti-termination system results in an increase in the percentage of FGF-5 present as full-length FGF-5, as shown by the data in the column labeled % FGF-5.

What is claimed is:

1. A vector for producing a polypeptide heterologous to prokaryotic cells comprising (1) anti-termination nucleic acid that inhibits intragenic transcription termination with a non-lambda promoter therefor, (2) DNA encoding the polypeptide with a non-lambda promoter therefor, wherein an RNA recognition site for binding anti-termination protein produced from the nucleic acid is located 5' of the DNA encoding the polypeptide, and (3) nucleic acid encoding a GreA or GreB protein with a promoter therefor.

2. The vector of claim 1 wherein the prokaryotic cells are bacterial cells.

3. The vector of claim 1 wherein the polypeptide is a mammalian polypeptide.

4. The vector of claim 1 wherein the non-lambda promoter is a trp or alkaline phosphatase promoter or both.

5. A process for increasing production of a full-length heterologous polypeptide as a percentage of total such heterologous polypeptide in prokaryotic host cells comprising:
(a) culturing the host cells, which comprise (1) anti-termination nucleic acid that inhibits intragenic transcription termination with a non-lambda promoter therefor, and (2) RNA encoding the polypeptide wherein the RNA is expressed from a gene with a non-lambda promoter therefor, wherein an RNA recognition site for binding anti-termination protein produced from the nucleic acid is located 5' of the RNA encoding the polypeptide, and wherein the anti-termination nucleic acid is expressed at the time of expression of the RNA; and
(b) recovering the heterologous polypeptide from the cells or from cell culture medium, whereby the amount of full-length heterologous polypeptide produced by the process is increased as a percentage of total said heterologous polypeptide produced.

6. The process of claim 5 wherein the heterologous polypeptide is a eukaryotic polypeptide.

7. The process of claim 6 wherein the heterologous polypeptide is a mammalian polypeptide.

8. The process of claim 7 wherein the mammalian polypeptide is a human polypeptide.

9. The process of claim 8 wherein the human polypeptide is thrombopoietin (TPO) or fibroblast growth factor-5 (FGF-5).

10. The process of claim 5 wherein the non-lambda promoter is a trp or alkaline phosphatase promoter or both.

11. The process of claim 5 wherein the RNA and anti-termination nucleic acid comprise a polycistronic genetic unit comprising a first cistron encoding the heterologous polypeptide and a second cistron downstream from the first cistron that is the anti-termination nucleic acid with a single promoter that controls transcription of said polycistronic genetic unit.

12. The process of claim 5 wherein the RNA and anti-termination nucleic acid are expressed under separate promoters.

13. The process of claim 5 wherein the prokaryotic cells are bacterial cells.

14. The process of claim 5 wherein the polypeptide is recovered from the cytoplasm or periplasm of the cells.

15. The process of claim 5 wherein the polypeptide is recovered from the cell culture medium.

16. The process of claim 5 wherein the anti-termination nucleic acid is a bacteriophage N or Q gene.

17. The process of claim 16 wherein the anti-termination nucleic acid is a lambda N gene.

18. The process of claim 17 wherein the RNA recognition site is a nut site.

19. The process of claim 18 wherein the nut site is lambda nutL, nutR, Box B, mutant nut, or nut from a lambdoid phage other than lambda phage.

20. The process of claim 5 wherein the host cells further comprise nucleic acid encoding a GreA or GreB protein with a promoter therefor.

21. The process of claim 20 wherein nucleic acid encoding GreB is expressed.

22. A process for increasing production of a full-length heterologous polypeptide as a percentage of total such heterologous polypeptide in prokaryotic host cells comprising:
(a) culturing the host cells, which comprise nucleic acid encoding GreA or GreB protein, nucleic acid encoding the heterologous polypeptide, and one or more promoters for the nucleic acids; and
(b) recovering the heterologous polypeptide from the cells or from cell culture medium, whereby the amount of full-length heterologous polypeptide produced by the process is increased as a percentage of total said heterologous polypeptide produced.

23. The process of claim 22 wherein nucleic acid encoding GreB protein is expressed.

24. The process of claim 22 wherein the cells are bacterial cells.

25. The process of claim 22 wherein the heterologous polypeptide is a mammalian polypeptide.

26. The process of claim 22 wherein the mammalian polypeptide is a human polypeptide.

27. The process of claim 26 wherein the human polypeptide is thrombopoietin (TPO) or fibroblast growth factor-5 (FGF-5).

28. The process of claim 22 wherein the promoter is a trp or alkaline phosphatase promoter or both.

29. The process of claim 22 wherein the polypeptide is recovered from the cytoplasm or periplasm of the cells.

30. The process of claim 22 wherein the polypeptide is recovered from the cell culture medium.

* * * * *